(12) United States Patent
Cowley et al.

(10) Patent No.: US 7,671,080 B2
(45) Date of Patent: Mar. 2, 2010

(54) 1-BENZYLINDOLE-2-CARBOXAMIDE DERIVATIVES

(75) Inventors: Phillip Martin Cowley, Newhouse (GB); Samuel George Gibson, Newhouse (GB); Grant Wishart, Newhouse (GB)

(73) Assignee: N.V. Organon, Oss (NL)

( * ) Notice: Subject to any disclaimer, the term of this patent is extended or adjusted under 35 U.S.C. 154(b) by 0 days.

(21) Appl. No.: 11/908,640

(22) PCT Filed: Mar. 17, 2006

(86) PCT No.: PCT/EP2006/060821

§ 371 (c)(1),
(2), (4) Date: Apr. 18, 2008

(87) PCT Pub. No.: WO2006/100208

PCT Pub. Date: Sep. 28, 2006

(65) Prior Publication Data

US 2008/0280923 A1    Nov. 13, 2008

(30) Foreign Application Priority Data

Mar. 21, 2005   (EP) .................................. 05102217

(51) Int. Cl.
*A61K 31/404* (2006.01)
*C07D 209/04* (2006.01)

(52) U.S. Cl. ...................... 514/415; 548/490
(58) Field of Classification Search ................. 514/415; 548/490
See application file for complete search history.

(56) References Cited

FOREIGN PATENT DOCUMENTS

WO    WO 01/58869    8/2001

OTHER PUBLICATIONS

Morissette et al. Advanced Drug Delivery Reviews 2004, 56, 275-300.*

Vippagunta, Sudha R. "Crystalline Solids." *Advanced Drug Delivery Reviews* 48(2001): 3-26.*

Hertzog, D.L., "Recent Advances in the cannabinoids," *Expert Opinion on Therapeutic Patents* 14 (2004) 1435-1452.

Howlett et al., "International Union of Pharmacology. XXVII. Classification of Cannabinoid Receptors," *Pharmacol Rev.* 54 (2002) 161-202.

Lange et al., "Recent advances in $CB_1$ Cannabinoid Receptor Antagonists," *Current Opinion In Drug Discovery And Development* 7 (2004) 498-506.

Sall, Daniel et al., "Use of Conformationally Restricted Benzamidines as Arginine Surrogates in the Design of Platelet GPIIb-IIIa Receptor Antagonists," *J. Med. Chem.* 40 (1997) 2843-2857.

* cited by examiner

*Primary Examiner*—Kamal A Saeed
*Assistant Examiner*—Samantha L Shterengarts
(74) *Attorney, Agent, or Firm*—Susan Hess

(57) ABSTRACT

The present invention relates to i-benzylindole-2-carboxamide derivatives of formula I, or a pharmaceutically acceptable salt or solvate thereof. The invention also relates to pharmaceutical compositions comprising said 1-benzylindole-2-carboxamide derivatives and to their use in therapy, particularly for the treatment of obesity or nicotine dependence.

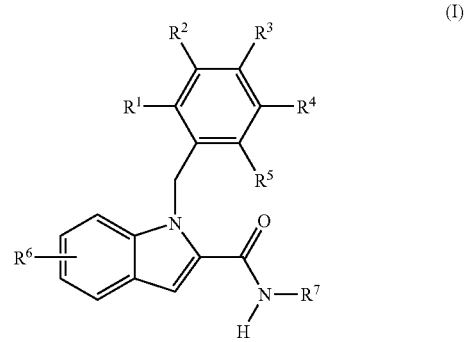

13 Claims, No Drawings

1-BENZYLINDOLE-2-CARBOXAMIDE DERIVATIVES

CROSS REFERENCE TO RELATED APPLICATION

This application claims priority based on International Patent Application No. PCT/EP2006/060821, filed on Mar. 17, 2006.

The present invention relates to 1-benzylindole-2-carboxamide derivatives, to pharmaceutical compositions comprising these compounds and to their use in therapy.

BACKGROUND OF THE INVENTION

Cannabis has been used as a medicinal agent for thousands of years leading to a large amount of research into the active components (the cannabinoids) and their receptors. Two types of cannabinoid receptors have recently been cloned and characterised. The canabinoid $CB_1$ receptor is located primarily in the central nervous system, but is also expressed by peripheral neurones and to a lower extent in other peripheral tissues. On the other hand the cannabinoid $CB_2$ receptor is mostly located in immune cells (Howlett A. C. et al., *Pharmacol Rev.* 2002, 54, 161-202). The background art of cannabinoid receptors and their ligands has been recently described in Hertzog D. L., *Expert Opinion on Therapeutic Patents*, 2004, 14, 1435-1452.

Several $CB_1$ receptor antagonists are known in the art. These compounds have been indicated to be useful in a variety of therapeutic applications including the treatment of obesity, nicotine dependence, drug addiction, asthma, liver cirrhosis, psychosis and memory and cognitive disorders (see Lange J. H. M. and Kruse C. G., *Current Opinion in Drug Discovery and Development*, 2004, 7, 498-506 for a recent review). In common with many cannabinoid ligands, the known compounds are lipophilic entities with relatively low water solubility. There remains a need for further $CB_1$ receptor antagonists which are safe and effective.

Recently indole-2-carboxamide derivatives were generically described in WO/0158869 (Bristol-Myers Squibb) as being active modulators of the cannabinoid receptor and as such useful in the treatment of respiratory diseases. WO/0158869, however, makes no specific disclosures of any 1-benzyl-indole-2-carboxamide derivatives.

DETAILED DESCRIPTION OF THE INVENTION

In a first aspect the present invention provides a 1-benzylindole-2-carboxamide derivative of formula I

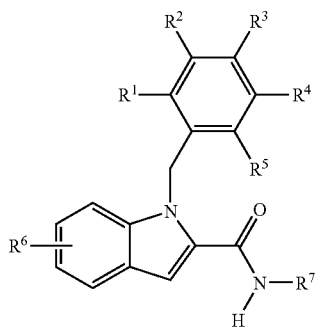

formula I wherein
$R^1$ is H or F;
$R^2$ is H, halogen, $C_{1-4}$alkyl, $C_{1-4}$alkyloxy, $C_{3-6}$cycloalkyl or $C_{3-6}$cycloalkylC$_{1-2}$alkyl, said $C_{1-4}$alkyl and $C_{1-4}$alkyloxy being optionally substituted with one to three halogens or $R^2$ is a five or six membered heteroaryl ring comprising one or two heteroatoms selected from N and O or $R^2$ is a five or six membered saturated heterocyclic ring comprising one or two heteroatomic moieties selected from O and $NR^8$;
$R^3$ is H or F;
$R^4$ is H, halogen, $CH_3$, $OCH_3$ or $CF_3$ or together with $R^5$ and the phenyl ring $R^4$ forms an indol-4-yl or a quinolin-5-yl;
$R^5$ is H, halogen, $C_{1-4}$alkyl, $CF_3$, $C_{1-4}$alkyloxy, $OCF_3$ or together with $R^4$ and the phenyl ring $R^5$ forms an indol-4-yl or a quinolin-5-yl;

provided that one to three of $R^1$-$R^5$ are not H;
$R^6$ is one or two substituents selected from Cl, Br and CN;
$R^7$ is $C_{1-6}$alkyl optionally substituted with one to three halogens, $C_{3-6}$cycloalkyl or $C_{3-6}$cycloalkylC$_{1-2}$alkyl each being substituted with one or two substituents selected from hydroxy, hydroxyC$_{1-2}$alkyl, $C_{1-4}$alkyloxy and $C_{1-2}$thioalkyloxy, or $R^7$ is $C_{4-6}$oxacycloalkylC$_{1-2}$alkyl, said $C_{1-2}$alkyl being optionally substituted with hydroxy or hydroxyC$_{1-2}$alkyl or $R^7$ is $C_{4-6}$oxacycloalkyl and
$R^8$ is H, $C_{1-4}$alkyl or $C_{1-4}$acyl or a pharmaceutically acceptable salt or solvate thereof.

The term $C_{1-6}$alkyl, as used herein, represents a branched or unbranched alkyl group having 1-6 carbon atoms. Examples of such groups are methyl, ethyl, isopropyl, tertiary butyl, pentyl and hexyl. Likewise the term $C_{1-4}$ alkyl, as used herein, represents a branched or unbranched alkyl group having 1-4 carbon atoms.

The term $C_{1-4}$ acyl, as used herein, represents an acyl group derived from a carboxylic acid having 1-4 carbon atoms. The acyl group can comprise a hydrocarbon which may be branched, unbranched, saturated or unsaturated. Examples of such groups include formyl, acetyl, propanoyl, propenoyl and pivaloyl. Also included within the definition of $C_{1-6}$ acyl are groups derived from dicarboxylic acids like hemi-malanoyl.

The term $C_{1-4}$alkyloxy, as used herein, represents a branched or unbranched alkyloxy group having 1-4 carbon atoms. Examples of such groups are methoxy, ethoxy, isopropyloxy and tertiary butyloxy. Similarly $C_{1-2}$alkyloxy, as used herein represents a branched or unbranched alkyloxy group having 1-2 carbon atoms The term $C_{3-6}$cycloalkyl, as used herein, represents a branched or unbranched cyclic alkyl group having 3-6 carbon atoms. Examples of such groups are cyclopropyl, cyclopentyl and 2-methylcyclopentyl. Similarly, the term $C_{4-6}$ cycloalkyl represents a branched or unbranched cyclic alkyl group having 4-6 carbon atoms.

The term $C_{3-6}$cycloalkylC$_{1-2}$alkyl, as used herein, represents a $C_{1-2}$ alkyl group which is substituted with a $C_{3-6}$cycloalkyl group. Examples of such rings are cyclopropylmethyl and 2-cyclobutylethyl.

The term hydroxyC$_{1-2}$alkyl, as used herein, represents a $C_{1-2}$alkyl group which is substituted with a hydroxyl group. Examples of such groups are hydroxymethyl and hydroxyethyl.

The term $C_{1-2}$thioalkyloxy, as used herein, represents a $C_{1-2}$alkyloxy group, wherein the oxygen atom is replaced by sulphur (i.e., a SC$_{1-2}$alkyl group). Examples of such groups are thiomethoxy and thioethoxy.

The term $C_{4-6}$oxacycloalkyl, as used herein, represents a branched or unbranched cyclic alkyl group having 4-6 carbon atoms in which one of the ring carbon atoms has been replaced by oxygen. Examples of such groups include tetrahydrofuranyl and 3-methyl tetrahydrofuranyl.

The term $C_{4-6}$oxacycloalkyl$C_{1-2}$alkyl, as used herein, represents a $C_{1-2}$alkyl group which is substituted with a $C_{4-6}$oxacycloalkyl group. Examples of such groups include tetrahydropyran-4-ylmethyl and 2-[3-methyltetrahydrofuran-2-yl] ethyl.

The term halogen, as used herein, represents a F, Cl, Br or I atom

Examples of five or six membered heteroaryl rings comprising one or two heteroatoms selected from N and O include furanyl, pyrrolyl, pyridinyl, oxazolyl, imidazolyl and pyrimidinyl.

Examples of five or six membered saturated heterocyclic rings comprising one or two heteroatomic moieties selected from O and $NR^8$, as used herein, wherein $R^8$ has the meaning as defined above include piperidinyl, homopiperidinyl, morpholinyl and 4-methylpiperazinyl.

In one embodiment of the present invention $R^1$ is H.

In another embodiment $R^2$ is $C_{1-4}$alkyl or $C_{1-4}$alkyloxy optionally substituted by halogen or halogen. In a further embodiment $R^2$ is $CH_3$, $CH(CH_3)_3$, $CF_3$, $OCH_3$, $OCH(CH_3)_2$, $OCHF_2$, $OCF_3$, Br, Cl or F. In a further embodiment $R^2$ is $CF_3$ or $OCF_3$.

In another embodiment $R^3$ is H.

In another embodiment $R^4$ is H, $CH_3$, $OCH_3$, F or Cl. In a further embodiment $R^4$ is H.

In another embodiment $R^5$ is H, $CH_3$, $OCH_3$, $OCF_3$, Cl or F. In a further embodiment $R^5$ is H, $CH_3$ or $OCH_3$.

In a further embodiment $R^1$, $R^3$ and $R^4$ are H.

In another embodiment $R^6$ is Cl.

In another embodiment $R^6$ is CN.

In a further embodiment $R^6$ is located at the 5-position of the indole ring.

In another embodiment $R^7$ is $C_{1-6}$alkyl optionally substituted with one to three halogens, $C_{3-6}$cycloalkyl or $C_{3-6}$cycloalkyl$C_{1-2}$alkyl substituted with one or two substituents selected from hydroxy, hydroxy$C_{1-2}$alkyl, $C_{1-4}$alkyloxy and $C_{1-2}$thioalkyloxy. In a further embodiment $R^7$ is $C_{1-6}$alkyl or $C_{3-6}$cycloalkyl$C_{1-2}$alkyl substituted with hydroxy or hydroxymethyl. In a further embodiment $R^7$ is $C_{4-6}$alkyl or $C_{4-6}$cycloalkyl$C_{1-2}$alkyl.

In a further embodiment $NHR^7$ is a group selected from:

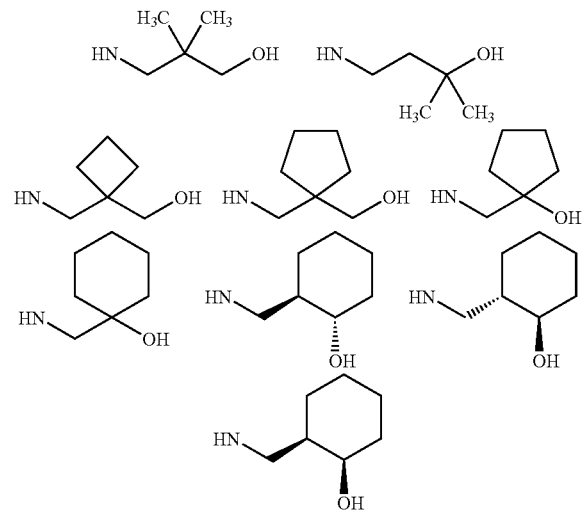

In another embodiment $R^7$ is $C_{4-6}$oxacycloalkyl$C_{1-2}$alkyl, said $C_{1-2}$alkyl being optionally substituted with hydroxy or hydroxy$C_{1-2}$alkyl.

In a further embodiment $R^7$ is $C_{4-6}$oxacycloalkyl.

In a further embodiment is a 1-(benzyl)-1H-indole-2-carboxylic acid amide derivative selected from:

5-chloro-1-(2,5-dimethylbenzyl)-1H-indole-2-carboxylic acid (3-hydroxy-2,2-dimethylpropyl)amide;

5-chloro-1-(2,5-bis-trifluoromethylbenzyl)-1H-indole-2-carboxylic acid (3-hydroxy-2,2-dimethylpropyl)amide;

5-chloro-1-(2-methoxy-5-trifluoromethoxybenzyl)-1H-indole-2-carboxylic acid (3-hydroxy-2,2-dimethylpropyl)amide;

5-cyano-1-(2-methoxy-5-trifluoromethoxybenzyl)-1H-indole-2-carboxylic acid (3-hydroxy-2,2-dimethylpropyl)amide;

5-cyano-1-(3-trifluoromethoxybenzyl)-1H-indole-2-carboxylic acid (3-hydroxy-2,2-dimethylpropyl)amide;

trans-5-cyano-1-(3-trifluoromethoxybenzyl)-1H-indole-2-carboxylic acid (2-hydroxy-cyclohexyl methyl)amide;

5-cyano-1-(5-bromo-2-methoxybenzyl)-1H-indole-2-carboxylic acid (3-hydroxy-2,2-dimethylpropyl)amide;

5-cyano-1-(5-tert-butyl-2-methoxybenzyl)-1H-indole-2-carboxylic acid (3-hydroxy-2,2-dimethylpropyl)amide;

5-cyano-1-(2-methoxy-5-methylbenzyl)-1H-indole-2-carboxylic acid (3-hydroxy-2,2-dimethylpropyl)amide;

5-cyano-1-(5-chloro-2-methoxybenzyl)-1H-indole-2-carboxylic acid (3-hydroxy-2,2-dimethylpropyl)amide;

5-cyano-1-(2-methyl-5-trifluoromethyl benzyl)-1H-indole-2-carboxylic acid (3-hydroxy-3-methylbutyl)amide;

5-cyano-1-(3-trifluoromethoxybenzyl)-1H-indole-2-carboxylic acid (1-hydroxymethylcyclopentylmethyl)amide and 5-cyano-1-(3-trifluoromethoxybenzyl)-1H-indole-2-carboxylic acid (1-hydroxymethylcyclobutylmethyl)amide.

The 1-(benzyl)-1H-indole-2-carboxylic acid amide derivatives of Formula I are prepared by methods well known in the art of organic chemistry, see for example, J. March, '*Advanced Organic Chemistry*' 4$^{th}$ Edition, John Wiley and Sons. For example, compounds of formula I can be prepared by the condensation of compounds of Formula II, wherein $R^1$-$R^6$ have the meanings as previously defined and C(O)X represents a carboxylic acid or an activated derivative thereof, such as a carboxylic acid halide, preferably a chloride or bromide, with amines of formula $NHR^7$, wherein $R^7$ has the meaning as previously defined. When C(O)X represents a carboxylic acid (i.e. X is hydroxy) the condensation reaction can be effected with the aid of a coupling agent, such as carbonyl diimidazole, dicyclohexylcarbodiimide and the like, in a solvent such as dimethylformamide or dichloromethane.

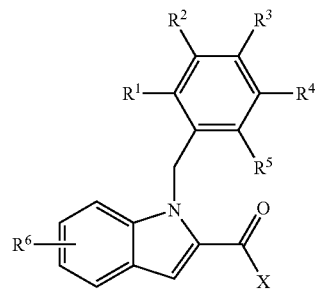

Formula II

When C(O)X represents a carboxylic acid halide (i.e X is halide) the condensation with the amine derivative II can be carried out in the presence of a base, for example triethylamine, in a solvent such as dichloromethane. The carboxylic acid halide, for example, a carboxylic acid chloride can be prepared by treatment of the corresponding carboxylic acid with, for example, oxalyl chloride or thionyl chloride in a solvent such as toluene or dichloromethane. Amines NHR$^7$ are obtained from commercial sources, prepared by literature procedures or modifications of literature procedures known to those persons skilled in the art, for example, through reduction of a nitrile using lithium aluminum hydride.

Compounds of formula II can be prepared by reaction of compounds of formula II, wherein R$^1$-R$^5$ are as defined previously and Y is a suitable leaving group, with compounds of formula IV, wherein R$^6$ is as defined previously and PG is a suitable protecting group, in the presence of a base such as sodium hydride. Suitable leaving groups are, for example, a halide or an alkyl sulphonate. Examples of conventional protecting groups are described in T. W. Greene and P. G. M. Wutts '*Protective Groups in Organic Synthesis*' 2$^{nd}$ Edition, John Wiley and Sons, 1991. For example, protection of PG as a carboxylic acid ester can be accomplished using methods well known in the art, for example, by reaction of the carboxylic acid with hydrogen chloride in ethanol at elevated temperatures. Following the reaction, the protecting group PG can be conveniently removed using methods also well known in the art, for example, where PG is a carboxylic acid ester, the unprotected carboxylic acid can be obtained by base-catalysed hydrolysis using sodium hydroxide, at elevated temperatures.

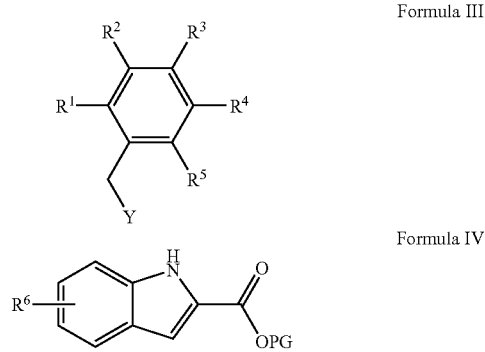

Formula III

Formula IV

Compounds of the formula III can be obtained from commercial sources, prepared by literature procedures or modifications of literature procedures known to those persons skilled in the art. For example, compounds of formula III can be prepared by halogenation of the related benzyl alcohol derivative using procedures well known in the art. For example, chlorination can be accomplished using, for example, thionyl chloride or oxalyl chloride and bromination can be accomplished using phosphorous tribromide or a combination of carbon tetrabromide and triphenylphosphine. The benzyl alcohols can be prepared by methods well known in the art, for example, by reduction of the corresponding benzoic acid ester using a reducing agent such as borane-tetrahydrofuran complex or lithium aluminium hydride.

Compounds of formula IV can be obtained from commercial sources, prepared by literature procedures or modifications of literature procedures known to persons skilled in the art, see for example WO 199639384 pages 100-101 and EP 0 655 439 A2 pages 34, 48-49 for the preparation of compounds wherein R$^6$ is CN.

The present invention also includes within its scope all stereoisomeric forms of compounds resulting because of configurational isomerism, such as enantiomers and diastereomers. For example, in the case where NHR$^7$ is 2-methyl-3-hydroxypropylamino the compound exists as a pair of enantiomers. In the case of individual enantiomers of compounds of formula I or salts or solvates thereof, the present invention includes a aforementioned enantiomer substantially free, i.e., associated with less than 5%, preferably less than 2% and in particular less than 1% of the other enantiomer. Mixtures of stereoisomers in any proportions, for example a racemic mixture comprising substantially equal amounts of two enantiomers are also included within the scope of the present invention.

For chiral compounds, methods for asymmetric synthesis whereby the pure stereoisomers are obtained are well known in the art, e.g., synthesis with chiral induction, synthesis starting from chiral intermediates, enantioselective enzymatic conversions, separation of stereoisomers using chromatography on chiral media. Such methods are described in *Chirality In Industry* (edited by A. N. Collins, G. N. Sheldrake and J. Crosby, 1992; John Wiley).

The 1-benzylindole-2-carboxamide derivatives of the present invention, in the form as a free base, are isolated from reaction mixtures as pharmaceutically acceptable salts. These salts are also obtained by treatment of said free base with an organic or inorganic acid such as hydrogen chloride, hydrogen bromide, hydrogen iodide, sulfuric acid, phosphoric acid, acetic acid, trifluoroacetic acid, propionic acid, glycolic acid, maleic acid, malonic acid, methanesulphonic acid, fumaric acid, succinic acid, tartaric acid, citric acid, benzoic acid and ascorbic acid. All salts, whether pharmaceutically acceptable or not are included within the scope of the present invention.

The 1-benzylindole-2-carboxamide derivatives of the present invention exist in both solvated and unsolvated forms, including hydrated forms. Both these forms are encompassed within the scope of the present invention.

The 1-benzylindole-2-carboxamide derivatives of the present invention also exist as amorphous forms. Multiple crystalline forms are also possible. All these physical forms are included within the scope of the present invention.

In a further aspect, the 1-benzylindole-2-carboxamide derivatives of the present invention are useful in therapy. In particular the 1-benzylindole-2-carboxamide derivatives of the present invention are useful in therapy in humans or animals. As such, the 1-benzylindole-2-carboxamide derivatives of the present invention are useful for the manufacture of a medicament for the treatment or prevention of disorders characterised by modulation of the activity of CB1 receptors.

In a further aspect the 1-benzylindole-2-carboxamide derivatives of the present invention are useful for the manufacture of a medicament for the treatment or prevention of appetite, weight gain, obesity, metabolic syndrome or diabetes. The skilled person will appreciate that such weight gain could be as a result of other drug treatment, such as treatment with an antipsychotic or antidepressant.

In a further aspect the 1-benzylindole-2-carboxamide derivatives of the present invention are useful for the manufacture of a medicament for the treatment or prevention of substance dependence or compulsive craving behaviours. The skilled person will appreciate that substance dependence can encompass numerous forms, such as dependence on nicotine or cigarette smoking, opioids (for example, heroin or morphine), stimulants (for example, cocaine or amphetamine), alcohol or cannabis. Treatment or prevention of substance dependence further includes aiding cessation of use, treatment of withdrawal symptoms (including craving and where problematic weight gain) and prevention of relapse in response to exposure to environmental or drug cues or stress.

In a further aspect the 1-benzylindole-2-carboxamide derivatives of the present invention are useful in the manufacture of a medicament for the treatment or prevention of impulsivity disorders.

In a still further aspect the 1-benzylindole-2-carboxamide derivatives of the subject invention are useful for the manufacture of a medicament for use in the treatment of cognitive disorders, schizophrenia or depression.

The present invention further includes a method for the treatment of a mammal, including a human, suffering from or liable to suffer from any of the aforementioned diseases or disorders, which method comprises administering an effective amount of a compound of the present invention or a pharmaceutically acceptable salt or solvate thereof.

The amount of a compound of the present invention or a pharmaceutically acceptable salt or solvate thereof, also referred to herein as the active ingredient, which is required to achieve a therapeutic effect will, of course, vary with the particular compound, the route of administration, the age and condition of the recipient, and the particular disorder or disease being treated.

A suitable daily dose for any of the above mentioned disorders will be in the range of 0.001 to 50 mg per kilogram body weight of the recipient (e.g. a human) per day, preferably in the range of 0.01 to 20 mg per kilogram body weight per day. The desired dose may be presented as multiple sub-doses administered at appropriate intervals throughout the day.

Whilst it is possible for the active ingredient to be administered alone, it is preferable to present it as a pharmaceutical formulation. The present invention therefore also provides a pharmaceutical composition comprising a compound according to the present invention in admixture with one or more pharmaceutically acceptable excipients, such as the ones described in Gennaro et. al., Remmington: *The Science and Practice of Pharmacy*, 20th Edition, Lippincott, Williams and Wilkins, 2000; see especially part 5: pharmaceutical manufacturing. Suitable excipients are described e.g., in the Handbook of Pharmaceutical Excipients, 2nd Edition; Editors A. Wade and P. J. Weller, American Pharmaceutical Association, Washington, The Pharmaceutical Press, London, 1994. Compositions include those suitable for oral, nasal, topical (including buccal, sublingual and transdermal), parenteral (including subcutaneous, intravenous and intramuscular) or rectal administration.

The mixtures of a compound according to the invention and one or more pharmaceutically acceptable excipient or excipients may be compressed into solid dosage units, such as tablets, or be processed into capsules or suppositories. By means of pharmaceutically suitable liquids the compounds can also be applied as an injection preparation in the form of a solution, suspension, emulsion, or as a spray, e.g., a nasal or buccal spray. For making dosage units e.g., tablets, the use of conventional additives such as fillers, colorants, polymeric binders and the like is contemplated. In general, any pharmaceutically acceptable additive can be used. The compounds of the invention are also suitable for use in an implant, a patch, a gel or any other preparation for immediate and/or sustained release.

Suitable fillers with which the pharmaceutical compositions can be prepared and administered include lactose, starch, cellulose and derivatives thereof, and the like, or mixtures thereof used in suitable amounts.

The invention is further illustrated by the following examples:

Example 1

5-Chloro-1-(3-methylbenzyl)-1H-indole-2-carboxylic acid (3-hydroxy-2,2-dimethylpropyl)amide

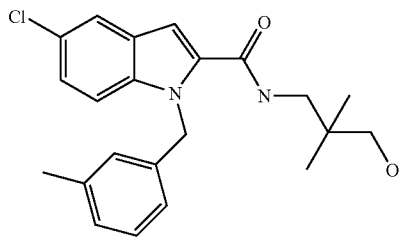

Sodium hydride (60% dispersion in mineral oil, 0.44 g, 7.45 mmol) was added to a suspension of 5-chloro-1H-indole-2-carboxylic acid ethyl ester (2.00 g, 8.94 mmol) in N,N'-dimethylformamide (DMF) (20 ml) under nitrogen. The mixture was stirred for 1 h before addition of the 3-methylbenzyl bromide (2.07 g, 2.48 ml) and the reaction stirred for 17.5 h. Water was added to reaction mixture which precipitated product as a gummy solid. Supernatant liquid was decanted and the solid washed with water. The product was dissolved in dichloromethane (DCM), washed with water, dried over magnesium sulfate and concentrated. Purification by silica chromatography using DCM as eluent, yielded 5-chloro-1-(3-methylbenzyl)-1H-indole-2-carboxylic acid ethyl ester (3.03 g, 95%).

A solution of 4M aqueous sodium hydroxide (0.29 ml) was added to a solution of 5-chloro-1-(3-methylbenzyl)-1H-indole-2-carboxylic acid ethyl ester (2.90 g, 8.85 mmol) in ethanol (30 ml) and the reaction heated at 45° C. for 3 h. After concentrating the mixture to 5 ml, a solution of 2M aqueous HCl (2 ml) was added to precipitate the product as a pale solid which was filtered, washed with water (3×30 ml) and dried under vacuum, to afford 5-chloro-1-(3-methylbenzyl)-1H-indole-2-carboxylic acid (2.57 g, 89%).

1-(3-Dimethylaminopropyl)-3-ethylcarbodiimide hydrochloride (EDCl) (0.14 g, 0.57 mmol) and 1-hydroxybenzotriazole hydrate (HOBT) (0.1 μg, 0.59 mmol) were added to a solution of 5-chloro-1-(3-methylbenzyl)-1H-indole-2-carboxylic acid (0.20 g, 0.67 mmol) in DCM (10 ml). After stirring for 10 min, 3-amino-2,2-dimethylpropan-1-ol (0.083 g, 0.80 mmol) was added. After stirring for 17.5 h, water (10 ml) was added, the layers separated, the organic phase washed with water (3×15 ml) and dried with magnesium sulfate. Purification was achieved by silica chromatography using DCM:methanol (3:1) as eluent. Crystallisation of the crude product afforded 5-chloro-1-(3-methylbenzyl)-1H-indole-2-carboxylic acid (3-hydroxy-2,2-dimethylpropyl)amide as a white solid (0.100 g, 43%).

$^1$H NMR (400 MHz, CDCl$_3$) $\delta_H$: 0.88 (s, 6H), 2.26 (s, 3H), 3.09 (br d, 2H, J=6.8), 3.25 (d, 2H, J=6.8), 3.45 (m, 1H), 5.74 (s, 2H), 6.54 (m, 1H), 6.77 (br d, 1H, J=7.8), 6.85 (s, 1H), 6.88 (s, 1H), 7.01 (br d, 1H, J=7.8), 7.11 (t, 1H, J=7.8), 7.22 (dd, 1H, J=8.8, 1.9), 7.30 (d, 1H, J=8.8) 7.61 (d, 1H, J=1.9);

EIMS: m/z=385.8 [M+H]$^+$.

Example 2

5-Chloro-1-(3-trifluoromethylbenzyl)-1H-indole-2-carboxylic acid (3-hydroxy-2,2-dimethylpropyl)amide

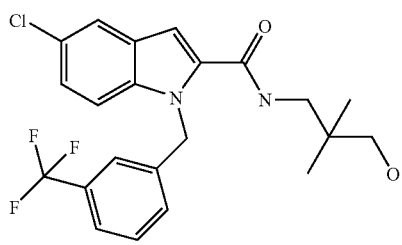

The title compound was prepared using 3-(trifluoromethyl)benzyl bromide in a manner similar to that described in Example 1.

$^1$H NMR (400 MHz, CDCl$_3$) δ$_H$: 0.89 (s, 6H), 3.13 (d, 2H, J=6.8), 3.24 (d, 1H, J=6.5), 3.26 (d, 2H, J=6.5), 5.83 (s, 2H), 6.67 (br t, 1H, J=6.5), 6.88 (s, 1H), 7.20 (d, 1H, J=7.8), 7.24 (m, 2H), 7.30 (br s, 1H), 7.36 (t, 1H, J=7.8), 7.47 (d, 1H, J=7.8), 7.64 (m, 1H);

EIMS: m/z=439.1 [M+H]$^+$.

Example 3

5-Chloro-1-(2-trifluoromethyl-5-fluorobenzyl)-1H-indole-2-carboxylic acid (3-hydroxy-2,2-dimethylpropyl)amide

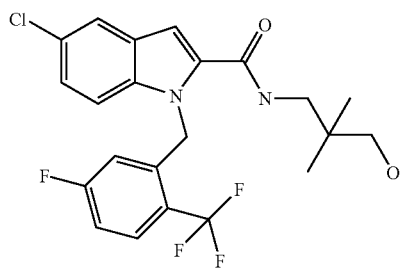

The title compound was prepared using 2-fluoro-5-(trifluoromethyl)benzyl bromide in a manner similar to that described in Example 1.

$^1$H NMR (400 MHz, CDCl$_3$) δ$_H$: 0.92 (s, 6H), 3.14 (dd, 1H, J=5.9, 7.2), 3.20 (m, 2H), 3.28 (d, 2H, J=6.0), 5.99 (br s, 1H), 6.09 (dd, 1H, J=10.0), 6.75 (br t, 1H, J=6.0), 6.95 (s, 1H), 6.98 (m, 1H), 7.09 (d, 1H, J=8.9), 7.20-7.24 (dd, 1H, J=8.9, 2.0), 7.67 (d, 1H, J=2.0), 7.70 (m, 1H);

EIMS: m/z=457.4 [M+H]$^+$.

Example 4

5-Chloro-1-(2,3,5-trifluorobenzyl)-1H-indole-2-carboxylic acid (3-hydroxy-2,2-dimethylpropyl)amide

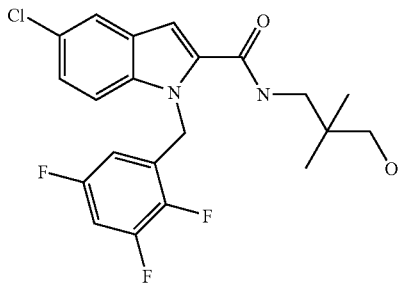

The title compound was prepared using 2,3,5-trifluorobenzyl bromide in a manner similar to that described in Example 1.

$^1$H NMR (400 MHz, CDCl$_3$) δ$_H$: 0.95 (s, 6H), 3.13 (m, 1H), 3.27 (d, 2H, J=6.3), 3.31 (d, 2H, J=6.5), 5.85 (s, 1H), 6.24 (m, 1H), 6.78 (m, 1H), 6.89 (s, 1H), 7.22 (d, 1H, J=8.8), 7.26 (dd, 1H, J=8.8, 1.8), 7.63 (d, 1H, J=1.8);

EIMS: m/z=425.0 [M+H]$^+$.

Example 5

5-Chloro-1-(2-methyl-3-fluorobenzyl)-1H-indole-2-carboxylic acid (3-hydroxy-2,2-dimethylpropyl)amide

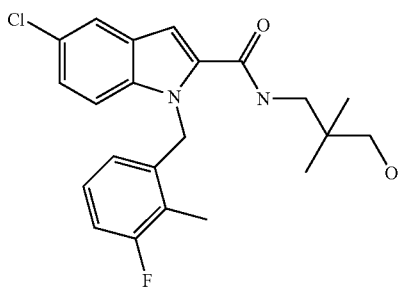

The title compound was prepared using 3-fluoro-2-methylbenzyl bromide in a manner similar to that described in Example 1.

$^1$H NMR (400 MHz, CDCl$_3$) δ$_H$: 0.86 (s, 1H), 2.32 (d, 3H, J=1.8), 3.05 (d, 2H, J=6.8), 3.22 (d, 2H, J=6.8), 3.28 (t, 1H, J=6.5), 5.77 (s, 1H), 5.95 (m, 1H), 6.61 (t, 1H, J=6.5), 6.88 (m, 2H), 6.89 (br s, 1H), 7.14 (d, 1H, J=8.8), 7.21 (d, 1H, J=8.8, 1.8), 7.65 (d, 1H, J=1.8);

EIMS: m/z=403.1 [M+H$^+$].

Example 6

5-Chloro-1-(3,4-difluorobenzyl)-1H-indole-2-carboxylic acid (3-hydroxy-2,2-dimethylpropyl)amide

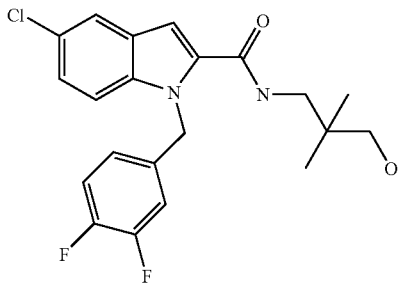

The title compound was prepared using 3,4-difluorobenzyl bromide in a manner similar to that described in Example 1.

$^1$H NMR (400 MHz, CDCl$_3$) δ$_H$: 0.92 (s, 6H), 3.19 (d, 2H, J=6.5), 3.28 (d, 2H, J=6.3), 3.28 (m, 3H), 5.72 (s, 1H), 6.69 (t, 1H, J=6.3), 6.80-6.86 (m, 2H), 6.87 (s, 1H), 7.05 (m, 1H), 7.25 (m, 2H), 7.63 (br s, 1H);

EIMS: m/z=407.1 [M+H]$^+$.

Example 7

5-Chloro-1-(2,5-bis-trifluoromethylbenzyl)-1H-indole-2-carboxylic acid (3-hydroxy-2,2-dimethylpropyl)amide

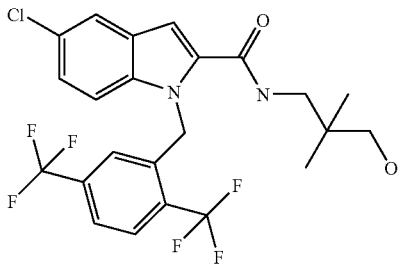

The title compound was prepared from 2,5-bis(trifluoromethyl)benzyl chloride in a manner similar to that described in Example 1.

$^1$H NMR (400 MHz, CDCl$_3$) δ$_H$: 0.90 (s, 6H), 3.11 (br s, 3H), 3.26 (d, 2H, J=6.5), 6.05 (br s, 2H), 6.63 (br s, 1H), 6.78 (br t, 1H, J=6.5), 6.98 (s, 1H), 7.10 (d, 1H, J=8.8), 7.23 (dd 1H, J=8.8, 1.9), 7.59 (d, 1H, J=8.2), 7.68 (d, 1H, J=1.9), 7.85 (d, 1H, J=8.2);

EIMS: m/z=507.0 [M+H]$^+$.

Example 8

5-Chloro-1-(2-methoxy-5-trifluoromethoxybenzyl)-1H-indole-2-carboxylic acid (3-hydroxy-2,2-dimethylpropyl)amide

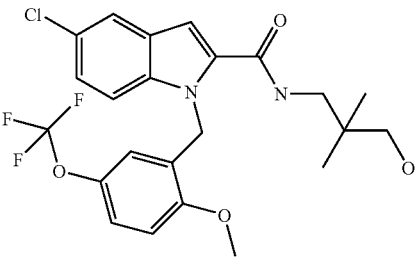

The title compound was prepared from 2-methoxy-5-(trifluoromethoxy)benzyl chloride in a manner similar to that described in Example 1.

$^1$H NMR (400 MHz, CDCl$_3$) δ$_H$: 0.89 (s, 6H), 3.06 (d, 2H, J=7.0), 3.34 (d, 2H, J=6.8), 3.37 (t, 1H, J=7.0), 3.90 (s, 1H), 5.78 (br s, 2H), 6.20 (d, 1H, J=2.3), 6.59 (br t, 1H, J=6.8), 6.85 (d, 1H, J=8.8), 6.88 (s, 1H), 7.03 (d, 2H, J=8.8, 2.3), 7.22 (m, 2H), 7.63 (br s, 1H);

EIMS: m/z=485.3 [M+H]$^+$.

Example 9

5-Chloro-1-(2,5-dimethylbenzyl)-1H-indole-2-carboxylic acid (3-hydroxy-2,2-dimethylpropyl)amide

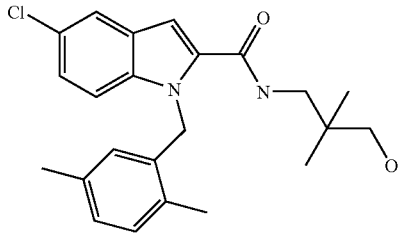

The title compound was prepared from 2-chloromethyl-1,4-dimethylbenzene in a manner similar to that described in Example 1.

$^1$H NMR (400 MHz, DMSO-d6) δ$_H$: 0.73 (s, 6H), 1.98 (s, 3H), 2.30 (s, 3H), 3.03 (d, 2H, J=5.7), 3.07 (d, 2H, J=6.3), 4.46 (t, 1H, J=5.7), 5.81 (s, 2H), 5.89 (s, 1H), 6.89 (d, 1H, J=7.5), 7.06 (d, 1H, J=7.5), 7.31 (s, 1H), 7.55 (d, 1H, J=8.4), 7.60 (d, 1H, J=8.4), 8.32 (s, 1H), 8.59 (t, 1H, J=6.3);

EIMS: m/z=398.9 [M+H]$^+$.

Example 10

5-Chloro-1-(2,5-dimethoxybenzyl)-1H-indole-2-carboxylic acid (3-hydroxy-2,2-dimethylpropyl)amide

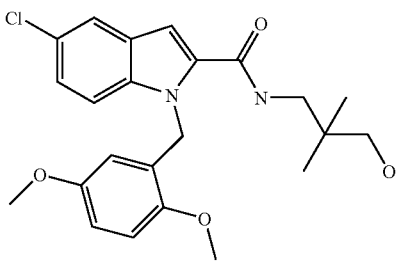

A solution of phosphorous tribromide (5.74 ml, 60.4 mmol) in anhydrous DCM (90 ml) was added over 20 min to a cooled, stirred solution of 2,5-dimethoxybenzyl alcohol (25.0 g, 148.8 mmol) in DCM (180 ml), maintaining the temperature between −5° C. and 0° C. Following the addition, the reaction was stirred at this temperature for a further 20 min. when water (200 ml) was added. After separation of the layers, the organic was washed with water (3×200 ml), dried with magnesium sulfate and evaporated to dryness under reduced pressure. The resulting crude product was crystallised from diethyl ether/heptane to afford 2-bromomethyl-1,4-dimethoxy-benzene (24.2 g, 72%).

The title compound was then prepared in a manner similar to that described in Example 1.

$^1$H NMR (400 MHz, CDCl$_3$) $\delta_H$: 0.88 (s, 6H), 3.08 (d, 2H, J=7.0), 3.25 (d, 2H, J=6.8), 3.52 (t, 1H, J=7.0), 3.57 (s, 3H), 3.84 (s, 3H), 5.75 (s, 2H), 6.03 (d, 1H, J=2.9), 6.59 (br t, 1H, J=6.8), 6.68 (dd, 1H, J=8.8, 2.9), 6.80 (d, 1H, J=8.8), 6.85 (s, 1H), 7.19 (dd, J=8.8, 1.9), 7.27 (m, 1H), 7.60 (d, 1H, J=1.9);

EIMS: m/z=431.3 [M+H]$^+$.

Example 11

5-Chloro-1-(5-tert-butyl-2-methoxybenzyl)-1H-indole-2-carboxylic acid (3-hydroxy-2,2-dimethylpropyl)amide

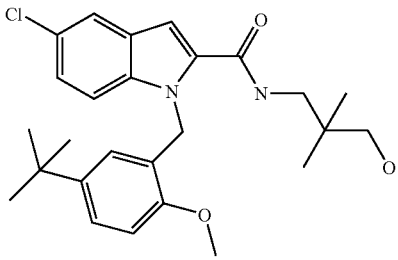

Hydrogen chloride gas was bubbled for 5 min into a stirred solution of 5-tert-butyl-2-methoxybenzoic acid (5.00 g, 24.0 mmol) in methanol (100 ml) at 0° C., after which time the solution was heated under reflux for 17.5 h. The reaction was cooled, evaporated to dryness under reduced pressure and purified by chromatography on silica using diethyl ether as eluent to afford 5-tert-butyl-2-methoxybenzoic acid methyl ester as a pale cream solid (5.06 g, 95%).

A solution of 1.0M lithium aluminium hydride in diethyl ether (27.0 ml, 27.0 mmol) was added dropwise over 10 min to a solution of 5-tert-butyl-2-methoxybenzoic acid methyl ester (5.00 g, 22.4 mmol) in diethyl ether (90 ml) under nitrogen, maintaining temperature between 0° C. and 5° C. When addition was complete, the reaction was stirred at 20° C. for 3.5 h, then again cooled to 0° C. Addition of water (5 ml) destroyed any excess reagent and filtration of the resulting mixture through dicalite removed the unwanted inorganic residue. After drying the resulting filtrate with magnesium sulfate, evaporation under reduced pressure afforded (5-tert-butyl-2-methoxyphenyl)methanol as a pale yellow gum (4.20 g, 21.6 mmol, 96%).

Triphenyl phosphine (5.84 g, 22.3 mmol) was added to a solution of (5-tert-butyl-2-methoxyphenyl)methanol (4.20 g, 21.8 mmol) in anhydrous DCM (80 ml) and the mixture cooled to 10° C. Carbon tetrabromide (7.39 g, 22.3 mmol) was added with stirring over 10 min, and after 30 min the temperature was raised to ambient temperature. Stirring continued for 17.5 h when the solvent was lowered to 20 ml under reduced pressure. Addition of heptane (80 ml) with stirring resulted in precipitation of triphenyl phosphine oxide, which was removed by filtration of the mixture through dicalite. Evaporation of the filtrate gave a straw coloured gum, purification of which was achieved by chromatography on silica using heptane:DCM (1:1) as eluent to afford 2-bromomethyl-4-tert-butyl-1-methoxybenzene as a clear gum (2.02 g, 36%).

Sodium hydride (60% dispersion in mineral oil, 0.154 g, 3.85 mmol) was added to a solution of 5-chloro-1H indole-2-carboxylic acid ethyl ester (0.70 g, 3.14 mmol) in dimethyl formamide (8 ml) with stirring under nitrogen, followed after 1 h by 2-bromomethyl-4-tert-butyl-1-methoxybenzene (1.00 g, 3.89 mmol). After stirring for 17 h, the reaction was diluted with water (15 ml), extracted into ethyl acetate (2×30 ml), washed with water (2×30 ml), dried with magnesium sulfate and evaporated to dryness under reduced pressure. Purification was achieved by chromatography on silica using DCM as eluent to yield 1-(5-tert-butyl-2-methoxybenzyl)-5-chloro-1H-indole-2-carboxylic acid ethyl ester as an off-white solid (1.18 g, 2.95 mmol, 94%).

A solution of 4M aqueous sodium hydroxide (1.10 ml) was added to a solution of 1-(5-tert-butyl-2-methoxybenzyl)-5-chloro-1H-indole-2-carboxylic acid ethyl ester (1.13 g, 2.82 mmol) in ethanol (15 ml) and the reaction heated at 45° C. for 3 h. After concentrating the mixture to 5.0 ml, a solution of 2M aqueous HCl (2.0 ml) was added to precipitate the product as a pale solid which was filtered, washed with water (3×30 ml) and dried under vacuum, affording 1-(5-tert-butyl-2-methoxybenzyl)-5-chloro-1H-indole-2-carboxylic acid (1.03 g, 2.77 mmol, 98%).

1-(3-Dimethylaminopropyl)-3-ethylcarbodiimide hydrochloride (0.11 g, 0.57 mmol) followed by 1-hydroxybenzotriazole hydrate (0.08 g, 0.59 mmol) were added to a solution of 1-(5-tert-butyl-2-methoxybenzyl)-5-chloro-1H-indole-2-carboxylic acid (0.20 g, 0.54 mmol) in DCM (10.0 ml) and after stirring for 10 min, 3-amino-2,2-dimethylpropan-1-ol (67 mg, 0.65 mmol) was added. After stirring for 17.5 h, water (10 ml) was added, the layers separated, the organic washed with water (3×15 ml) and dried with magnesium sulfate. Purification was achieved by chromatography on silica using DCM:methanol (3:1) as eluent. Crystallisation of the crude afforded the title compound as a white solid (90 mg, 36%).

$^1$H NMR (400 MHz, CDCl$_3$) $\delta_H$: 0.88 (s, 6H), 1.07 (s, 9H), 3.08 (d, 2H, J=6.8), 3.25 (d, 2H, J=7.0), 3.46 (t, 1H, J=7.0), 3.83 (s, 3H), 5.77 (s, 2H), 6.52 (m, 2H), 6.78 (d, 1H, J=8.5), 6.85 (s, 1H), 7.14-7.20 (m, 2H), 7.31 (d, 1H, J=8.8), 7.60 (d, 1H, J=1.8);

EIMS: m/z=457.1 [M+H]$^+$.

Example 12

5-Chloro-1-(2-methoxy-5-bromobenzyl)-1H-indole-2-carboxylic acid (3-hydroxy-2,2-dimethyl-propyl)amide

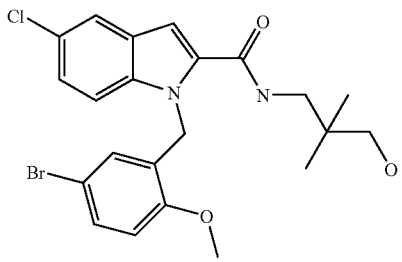

The title compound was prepared using 2-methoxy-5-bromobenzyl alcohol in a manner similar to that described in Example 11.

$^1$H NMR (400 MHz, CDCl$_3$) $\delta_H$: 0.90 (s, 6H), 3.07 (br s, 2H), 3.25 (d, 2H, J=6.6), 3.45 (br s, 1H), 3.87 (s, 3H), 5.74 (s, 2H), 6.47 (d, 1H, J=2.5), 6.64 (t, 1H, J=6.6), 6.75 (d, 1H, J=8.8), 6.88 (s, 1H), 7.20-7.24 (m, 2H), 7.27 (dd, 1H, J=8.8, 2.5), 7.63 (br s, 1H);

EIMS: m/z=481.0 [M+H]$^+$.

Example 13

5-Chloro-1-(2-methoxy-5-methylbenzyl)-1H-indole-2-carboxylic acid (3-hydroxy-2,2-dimethylpropyl)amide

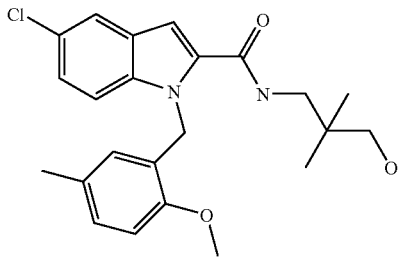

The title compound was prepared from 5-methyl-2-methoxybenzoic acid in a manner similar to that described in Example 11.

$^1$H NMR (400 MHz, CDCl$_3$) $\delta_H$: 0.88 (s, 6H), 2.08 (s, 3H), 3.08 (d, 2H, J=7.0), 3.25 (d, 2H, J=6.8), 3.47 (m, 1H), 3.83 (s, 3H), 5.73 (s, 2H), 6.30 (d, 1H, J=1.7), 6.55 (s, 1H), 6.76 (d, 1H, J=8.3), 6.85 (s, 1H), 6.96 (dd, 1H, J=8.3, 1.7), 7.19 (dd, 1H J=8.8, 1.9), 7.29 (d, 1H, J=8.8), 7.61 (d, 1H, J=1.9);

EIMS: m/z=415.0 [M+H]$^+$.

Example 14 trans-5-Chloro-1-(3-trifluoromethoxybenzyl)-1H-indole-2-carboxylic acid (2-hydroxy-cyclohexylmethyl)amide

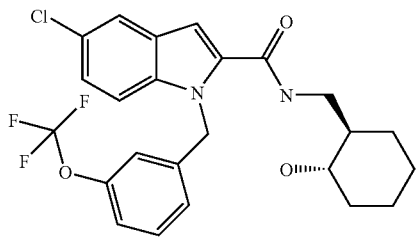

The title compound was prepared from 3-trifluoromethoxybenzyl bromide and trans-2-aminomethyl-1-cyclohexanol in a manner similar to that described in Example 1.

$^1$H NMR (400 MHz, CDCl$_3$) $\delta_H$: 0.86-1.35 (m, 4H), 1.40-1.49 (m, 1H), 1.63-1.70 (m, 2H), 1.70-1.77 (m, 1H), 1.88-1.95 (m, 1H), 2.98 (ddd, 1H, J=14.1, 5.5, 4.0), 3.06-3.15 (m, 2H), 3.99 (ddd, 1H, J=13.8, 8.5, 3.5), 5.80, 5.83 (ABq, 2H, J=16.5), 6.85 (s, 1H), 6.86 (s, 1H), 6.93-6.98 (m, 2H), 7.04-7.08 (m, 1H), 7.23-7.29 (m, 3H), 7.62 (br t, 1H, J=1.4);

EIMS: m/z=481.2 [M+H]$^+$, 503.0 [M+Na]$^+$.

Example 15

5-Chloro-1-(3-trifluoromethoxybenzyl)-1H-indole-2-carboxylic acid (3-isopropoxypropyl)amide

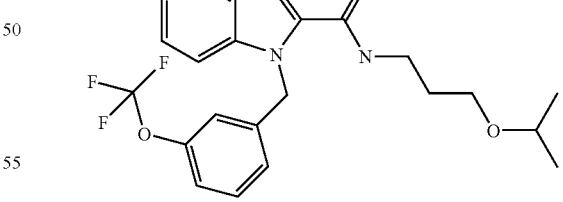

The title compound was prepared from 3-trifluoromethoxybenzyl bromide and ethyl 3-isopropoxypropylamine in a manner similar to that described in Example 1.

$^1$H NMR (400 MHz, CDCl$_3$) $\delta_H$: 1.19 (s, 3H), 1.21 (s, 3H), 1.85 (quint, 2H, J=5.8), 3.51-3.63 (m, 5H), 5.84 (s, 2H), 6.83 (s, 1H), 6.91 (br s, 1H), 6.96 (br d, 1H, J=7.9), 7.06 (d br t, 1H, J=7.9, 1.3), 7.20 (s, 1H), 7.21 (s, 1H), 7.26 (t, 1H, J=7.9), 7.32 (br t, 1H), 7.62 (t, 1H, J=1.3);

EIMS: m/z=469.5 [M+H]$^+$.

Example 16

5-Chloro-1-(3-trifluoromethoxybenzyl)-1H-indole-2-carboxylic acid (1-hydroxy-cyclohexylmethyl)amide

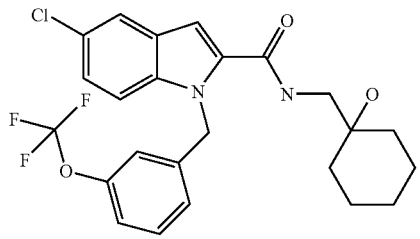

The title compound was prepared from 3-trifluoromethoxybenzyl bromide and 1-aminomethyl-1-cyclohexanol hydrochloride in a manner similar to that described in Example 1.

$^1$H NMR (400 MHz, MeOD) $\delta_H$: 1.22-1.67 (m, 10H), 3.34 (br s, 2H), 5.85 (s, 2H), 6.91 (br s, 1H), 7.00 (br d, 1H, J=8.0), 7.10 (br d, 1H, J=8.0), 7.13 (s, 1H), 7.23 (dd, 1H, J=8.8, 2.0), 7.32 (t, 1H, J=8.0), 7.42 (d, 1H, J=8.8), 7.67 (d, 1H, J=2.0); EIMS: m/z=481.3 [M+H]$^+$.

Example 17

5-Chloro-1-(3-trifluoromethoxybenzyl)-1H-indole-2-carboxylic acid (3-hydroxy-3-methylbutyl)amide

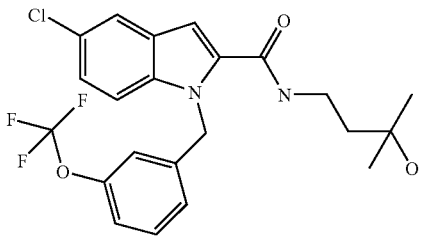

A solution of 3.0M methyl magnesium bromide in diethyl ether (0.5 ml, 1.50 mmol) was added dropwise to a solution of 3-{[5-chloro-1-(3-trifluoromethoxybenzyl)-1H-indole-2-carbonyl]amino}propionic acid ethyl ester (Example 15) (200 mg, 0.42 mmol) in THF (4 ml) under nitrogen, maintaining temperature between 0 and 5° C. After stirring at 0° C. for 2 h, the reaction was quenched by slowly pouring the reaction mixture into water (2.0 ml). Volatile solvents were then removed under reduced pressure and the aqueous residue filtered. Purification was achieved by chromatography on silica using heptane:ethyl acetate (9:1 followed by 4:1) as eluent to afford 5-chloro-1-(3-trifluoromethoxybenzyl)-1H-indole-2-carboxylic acid (3-hydroxy-3-methylbutyl)amide as an off-white solid (28 mg, 15%).

$^1$H NMR (400 MHz, CDCl$_3$) $\delta_H$: 1.31 (s, 6H), 1.56 (t, 2H, J=6.2), 3.57 (q, 2H, J=6.2), 5.83 (s, 2H), 6.82 (s, 1H), 6.92 (br s, 1H), 6.96 (d, 1H, J=8.0), 7.05 (d, 1H, J=8.0), 7.20 (m, 2H), 7.25 (t, 1H, J=7.9), 7.29 (t, 1H, J=8.0), 7.60 (t, 1H, J=1.3); EIMS: m/z=455.2 [M+H]$^+$.

Example 18

5-Cyano-1-(2,5-dimethylbenzyl)-1H-indole-2-carboxylic acid (3-hydroxy-2,2-dimethylpropyl)amide

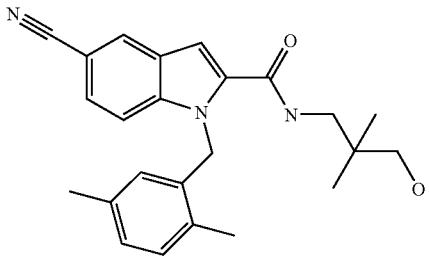

The title compound was prepared from 2-chloromethyl-1,4-dimethylbenzene and 5-cyano-1H-indole-2-carboxylic acid, (prepared according to literature method—see, for example, WO 199639384 pages 100-101 and EP 0 655 439 A2 pages 34, 48-49) in a manner similar to that described in Example 1.

$^1$H NMR (DMSO-d6) $\delta_H$: 0.72 (s, 6H), 1.98 (s, 3H), 2.30 (s, 3H), 3.03 (d, 2H, J=5.7), 3.07 (d, 2H, J=6.3), 4.47 (t, 1H, J=5.7), 5.81 (s, 2H), 5.88 (s, 1H), 6.89 (d, 1H, J=7.5), 7.06 (d, 1H, J=7.5), 7.31 (s, 1H), 7.56 (dd, 1H, J=8.5, 1.3), 7.59 (d, 1H, J=8.5) 8.59 (t, 1H, J=6.3); EIMS: m/z=390.0 [M+H]$^+$.

Example 19

5-Cyano-1-(2-methoxybenzyl)-1H-indole-2-carboxylic acid (3-hydroxy-2,2-dimethylpropyl)amide

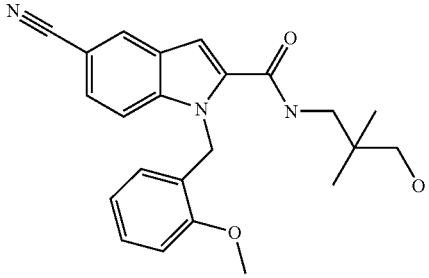

The title compound was prepared from 2-methoxybenzyl chloride in a manner similar to that described in Example 18.

$^1$H NMR (400 MHz, CDCl$_3$) $\delta_H$: 0.89 (s, 6H), 3.11 (s, 2H), 3.27 (d, 2H, J=6.5), 3.86 (s, 3H), 5.81 (s, 2H), 6.49 (d, 1H, J=7.5), 6.66 (br t, 1H, J=6.5), 6.74 (t, 1H, J=7.5), 6.87 (d, 1H, J=8.2), 6.97 (s, 1H), 7.19 (dt, 1H, J=7.5, 1.5), 7.43 (d, 1H, J=8.6), 7.46 (dd, 1H, J=8.6, 1.4), 8.00 (s, 1H); EIMS: m/z=392.3 [M+H]$^+$.

Example 20

5-Cyano-1-(3,5-dimethylbenzyl)-1H-indole-2-carboxylic acid (3-hydroxy-2,2-dimethylpropyl)amide

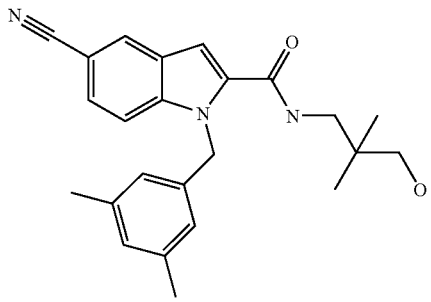

The title compound was prepared using 3,5-dimethylbenzyl bromide in a manner similar to that for Example 18.

$^1$H NMR (400 MHz, CDCl$_3$) $\delta_H$: 0.89 (s, 6H), 2.21 (s, 6H), 3.12 (d, 2H, J=6.8), 3.28 (d, 2H, J=6.3), 3.32 (t, 1H, J=6.8), 5.74 (s, 2H), 6.64 (br s, 2H), 6.68 (t, 1H, J=6.3), 6.85 (br s, 1H), 6.98 (s, 1H), 7.45 (d, 1H, J=8.8), 7.49 (dd, J=8.8, 1.5), 8.02 (br s, 1H);

EIMS: m/z=390.4 [M+H]$^+$.

Example 21

5-Cyano-1-(4-fluoro-benzyl)-1H-indole-2-carboxylic acid (3-hydroxy-2,2-dimethylpropyl)amide

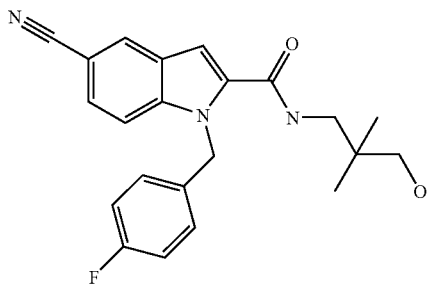

The title compound was prepared using 4-fluorobenzyl bromide in a manner similar to that described in Example 18.

$^1$H NMR (400 MHz, CDCl$_3$) $\delta_H$: 0.91 (s, 6H), 3.19 (s, 2H), 3.29 (d, 2H, J=6.3), 5.78 (s, 2H), 6.76 (br t, 1H, J=6.3), 6.90-7.00 (m, 3H), 7.02-7.08 (m, 2H), 7.43 (d, 1H, J=8.6, 1.5), 7.50 (dd, 1H, J=8.6, 1.5), 8.02 (br s, 1H);

EIMS: m/z=380.3 [M+H]$^+$.

Example 22

5-Cyano-1-(2-methoxy-5-trifluoromethoxybenzyl)-1H-indole-2-carboxylic acid (3-hydroxy-2,2-dimethylpropyl)amide

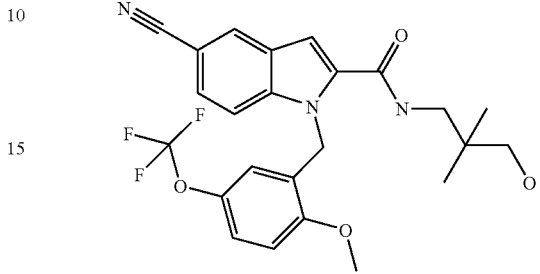

The title compound was prepared using 2-methoxy-5-trifluoromethoxy benzyl bromide in a manner similar to that for Example 18.

$^1$H NMR (400 MHz, CDCl$_3$): $\delta_H$: 0.90 (s, 6H), 3.13 (s, 2H), 3.28 (d, 2H, J=6.5), 3.89 (s, 3H), 5.82 (s, 2H), 6.28 (d, 1H, J=1.8), 6.80 (br t, 1H, J=6.5), 6.86 (d, 1H, J=8.9), 7.01 (s, 1H), 7.05 (dd, 1H, J=8.9, 1.8), 7.40 (d, 1H, J=8.8), 7.48 (dd, 1H, J=8.8, 1.3), 8.02 (br s, 1H);

EIMS: m/z=476.0 [M+H]$^+$.

Example 23

5-Cyano-1-(3-trifluoromethoxybenzyl)-1H-indole-2-carboxylic acid (3-hydroxy-2,2-dimethylpropyl)amide

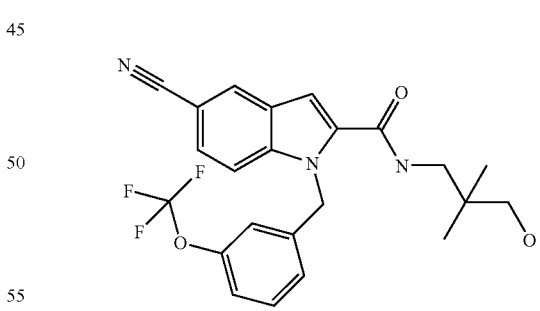

The title compound was prepared using 3-trifluoromethoxybenzyl bromide in a manner similar to that described in Example 18.

$^1$H NMR (400 MHz, CDCl$_3$) $\delta_H$: 0.90 (s, 6H), 3.18 (s, 2H), 3.29 (d, 2H, J=6.2), 5.84 (s, 2H), 6.80 (br t, 1H, J=6.2), 6.84 (br s, 1H), 6.99 (br d, 1H, J=7.9), 7.01 (s, 1H), 7.08 (br d, 1H, J=7.9), 7.29 (t, 1H, J=7.9), 7.40 (d, 1H, J=8.7), 7.50 (dd, 1H, J=8.7, 1.4), 8.03 (d, 1H, J=1.4);

EIMS: m/z=446.0 [M+H]$^+$.

Example 24

5-Cyano-1-(2,5-dichlorobenzyl)-1H-indole-2-carboxylic acid (3-hydroxy-2,2-dimethylpropyl)amide

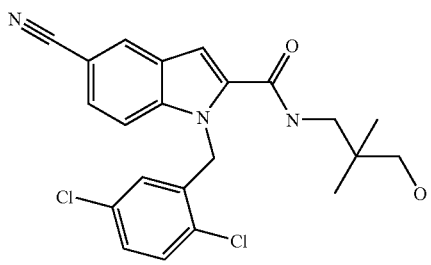

The title compound was prepared using 2,5-dichlorobenzyl bromide in a manner similar to that described in Example 18.

$^1$H NMR (400 MHz, CDCl$_3$) δ$_H$: 0.93 (s, 6H), 3.01 (t, 1H, J=6.4), 3.23 (d, 2H, J=6.4), 3.28 (d, 2H, J=6.2), 5.88 (s, 2H), 6.37 (d, 1H, J=2.4), 6.91 (br t, 1H, J=6.2), 7.06 (s, 1H), 7.16 (dd, 1H, J=6.0, 2.4), 7.31 (d, 1H, J=8.4), 7.34 (d, 1H, J=8.4), 7.50 (dd, 1H, J=8.5, 2.4), 8.05 (br s, 1H);

EIMS: m/z=430.0, 432.4 [M+H]$^+$.

Example 25

5-Cyano-1-(3-fluoro-5-trifluoromethylbenzyl)-1H-indole-2-carboxylic acid (3-hydroxy-2,2-dimethylpropyl)amide

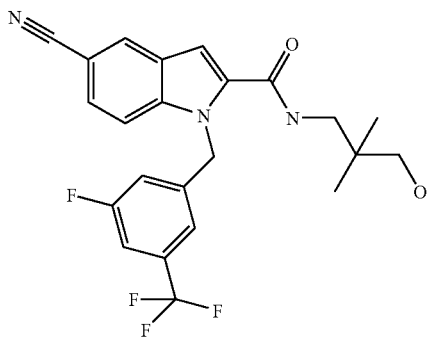

The title compound was prepared using 3-fluoro-5-trifluoromethylbenzyl bromide in a manner similar to that described in Example 18.

$^1$H NMR (400 MHz, CDCl$_3$) δ$_H$: 0.94 (s, 6H), 2.92 (t, 1H, J=6.2), 3.25 (d, 2H, J=6.5), 3.31 (d, 2H, J=6.5), 5.29 (s, 1H), 6.03 (s, 2H), 6.10 (dd, 1H, J=9.3, 1.8), 6.90-7.04 (m, 2H), 7.08 (s, 1H), 7.48 (d, 1H, J=8.7), 7.72 (m, 1H), 8.07 (s, 1H);

EIMS: m/z=448.0 [M+H]$^+$.

Example 26

5-Cyano-1-(2-methylbenzyl)-1H-indole-2-carboxylic acid (3-hydroxy-2,2-dimethylpropyl)amide

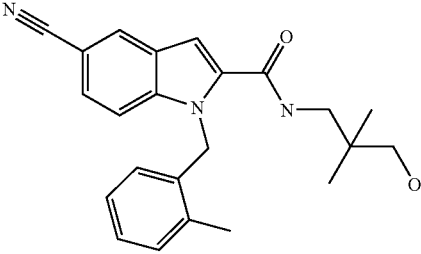

The title compound was prepared using 2-methylbenzyl bromide in a manner similar to that described in Example 18.

$^1$H NMR (400 MHz, CDCl$_3$) δ$_H$: 0.84 (s, 6H), 2.41 (s, 3H), 3.01 (d, 2H, J=5.8), 3.10-3.19 (m, 1H), 3.22 (d, 2H, J=6.5), 5.80 (s, 2H), 6.13 (d, 1H, J=7.5), 6.66 (br s, 1H), 6.93 (t, 1H, J=7.5), 7.01 (s, 1H), 7.12 (t, 1H, J=7.5), 7.19 (d, 1H, J=7.5), 7.31 (d, 1H, J=8.7), 7.46 (dd, 1H, J=8.7, 1.5), 8.04 (br s, 1H);

EIMS: m/z=376.5 [M+H]$^+$.

Example 27

5-Cyano-1-(2-trifluoromethoxybenzyl)-1H-indole-2-carboxylic acid (3-hydroxy-2,2-dimethylpropyl)amide

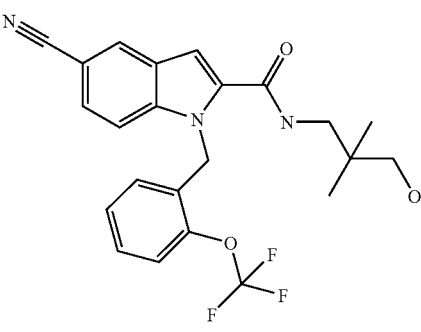

The title compound was prepared using 2-(trifluoromethoxy)benzyl bromide in a manner similar to that described in Example 18.

$^1$H NMR (400 MHz, CDCl$_3$) δ$_H$: 0.92 (s, 6H), 3.01 (t, 1H, J=6.5), 3.22 (d, 2H, J=6.5), 3.30 (d, 2H, J=6.5), 5.90 (s, 2H), 6.59 (d, 1H, J=8.2), 6.82 (ddd, 1H, J=8.2, 6.0, 2.8), 7.01 (s, 1H), 7.09 (m, 1H), 7.28 (m, 3H), 7.47 (dd, 1H, J=8.7, 1.5), 8.03 (br s, 1H);

EIMS: m/z=446.0 [M+H]$^+$.

Example 28

5-Cyano-1-(2-fluoro-3-methylbenzyl)-1H-indole-2-carboxylic acid (3-hydroxy-2,2-dimethylpropyl) amide

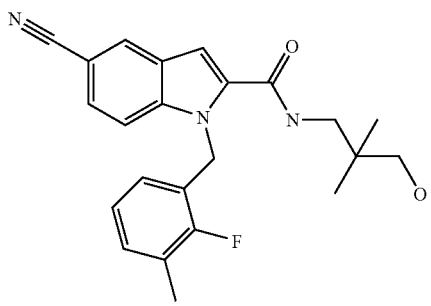

The title compound was prepared using 2-fluoro-3-methylbenzyl bromide in a manner similar to that described in Example 18.

$^1$H NMR (400 MHz, CDCl$_3$) δ$_H$: 0.92 (s, 6H), 2.26 (d, 3H, J=1.5), 3.21 (s, 2H), 3.31 (d, 2H, J=6.4), 5.87 (s, 2H), 6.58 (br t, 1H, J=7.3), 6.80 (br t, 1H, J=6.4), 6.85 (t, 1H, J=7.5), 6.98 (s, 1H), 7.05 (t, 1H, J=7.3), 7.43 (d, 1H, J=8.7), 7.48 (dd, 1H, J=8.7, 1.4), 8.00 (s, 1H);

EIMS: m/z=394.0 [M+H]$^+$.

Example 29

5-Cyano-1-(2-bromobenzyl)-1H-indole-2-carboxylic acid (3-hydroxy-2,2-dimethylpropyl)amide

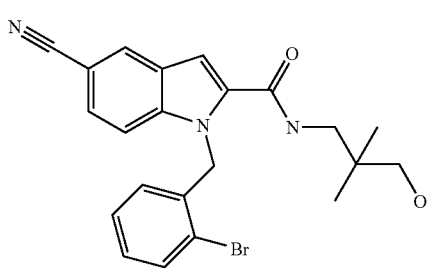

The title compound was prepared using 2-bromobenzyl bromide in a manner similar to that described in Example 18.

$^1$H NMR (400 MHz, CDCl$_3$): δ$_H$: 0.91 (s, 6H), 3.17 (d, 2H, J=5.2), 3.18 (s, 1H), 3.28 (d, 2H, J=6.5), 5.88 (s, 2H), 6.30 (m, 1H), 6.83 (m, 1H), 7.05 (s, 1H), 7.08 (m, 2H), 7.30 (d, 1H, J=8.8), 7.47 (d, 1H, J=8.5), 7.60 (d, 1H, J=7.2), 8.05 (s, 1H);

EIMS: m/z=440.0, 442.0 [M+H]$^+$.

Example 30

5-Cyano-1-(3,5-dimethoxybenzyl)-1H-indole-2-carboxylic acid (3-hydroxy-2,2-dimethylpropyl) amide

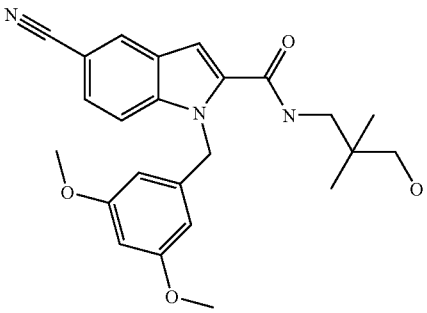

The title compound was prepared using 3,5-dimethoxybenzyl bromide in a manner similar to that described in Example 18.

$^1$H NMR (400 MHz, CDCl$_3$) δ$_H$: 0.90 (s, 6H), 3.13 (d, 2H, J=6.7), 3.31 (d, 2H, J=6.6), 3.35 (t, 1H, J=6.7), 3.70 (s, 6H), 5.75 (s, 2H), 6.15 (d, 2H, J=2.2), 6.31 (t, 1H, J=2.3), 6.74 (br t, 1H, J=6.6), 6.98 (s, 1H), 7.43 (d, 1H, J=8.7), 7.48 (dd, 1H, J=8.7, 1.5), 8.00 (br s, 1H);

EIMS: m/z=422.1 [M+H]$^+$.

Example 31

5-Cyano-1-(3-difluoromethoxybenzyl)-1H-indole-2-carboxylic acid (3-hydroxy-2,2-dimethylpropyl) amide

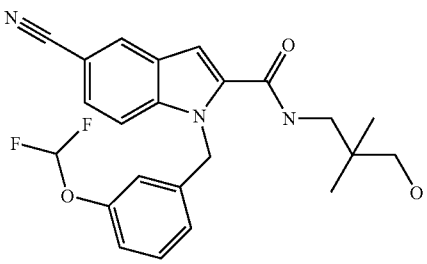

The title compound was prepared using 3-(difluoromethoxy)benzyl bromide in a manner similar to that described in Example 18.

$^1$H NMR (400 MHz, CDCl$_3$) δ$_H$: 0.90 (s, 6H), 3.10-3.18 (m, 2H), 3.18-3.22 (m, 1H), 3.28 (d, 2H, J=7.2), 5.82 (s, 2H), 6.46 (t, 1H, J=73.8), 6.75-6.80 (m, 2H), 6.87 (br d, 1H, J=8.0), 6.98 (dd, 1H, J=8.0, 2.0), 7.01 (s, 1H), 7.25 (t, 1H, J=8.0), 7.41 (d, 1H, J=8.4), 7.51 (dd, 1H, J=8.8, 1.6), 8.04 (br s, 1H);

EIMS: m/z=428.1 [M+H]$^+$.

Example 32

5-Cyano-1-quinolin-8-yl-methyl-1H-indole-2-carboxylic acid (3-hydroxy-2,2-dimethylpropyl)amide

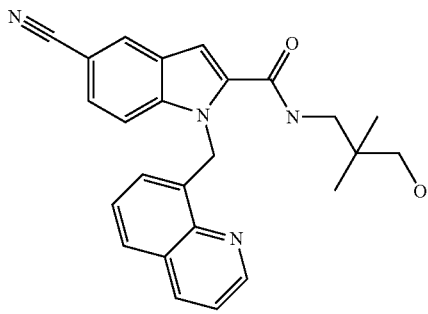

The title compound was prepared using 8-(bromomethyl)quinoline in a manner similar to that described in Example 18.

$^1$H NMR (400 MHz, CDCl$_3$) δ$_H$: 0.90 (s, 6H), 3.16-3.20 (m, 2H), 3.22-3.26 (m, 1H), 3.30 (d, 2H, J=6.5), 6.49 (s, 2H), 7.00 (d, 1H, J=7.1), 7.04 (s, 1H), 7.13 (br t, 1H, J=6.5), 7.33-7.45 (m, 3H), 7.47 (dd, 1H, J=8.3, 4.3), 7.73 (d, 1H, J=8.3), 8.01 (br s, 1H), 8.18 (dd, 1H, J=8.3, 1.8), 8.97 (dd, 1H, J=4.3, 1.8);

EIMS: m/z=413.1 [M+H]$^+$.

Example 33 trans-5-Cyano-1-(3,5-dimethoxybenzyl)-1H-indole-2-carboxylic acid (2-hydroxy-cyclohexylmethyl)amide

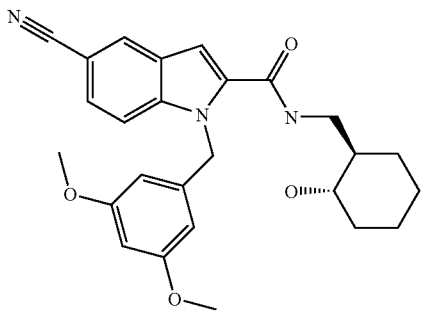

The title compound was prepared using 3,5-dimethoxybenzyl bromide and trans-2-aminomethyl-1-cyclohexanol in a manner similar to that described in Example 18.

$^1$H NMR (400 MHz, CDCl$_3$) δ$_H$: 0.95-1.33 (m, 3H), 1.39-1.48 (m, 1H), 1.62-1.77 (s, 3H), 1.87-1.94 (m, 1H), 2.94-3.01 (m, 1H), 3.05-3.12 (m, 2H), 3.70 (s, 6H), 3.96-4.04 (m, 1H), 5.73, 5.80 (ABq, 2H, J=16.3), 6.15 (d, 2H, J=2.3), 6.30 (t, 1H, J=2.3), 6.95 (s, 1H), 7.01 (m, 1H), 7.42 (d, 1H, J=8.8), 7.47 (dd, 1H, J=8.8, 1.5), 7.99 (m, 1H);

EIMS: m/z=447.7 [M+H]$^+$.

Example 34 trans-5-Cyano-1-(3-trifluoromethoxybenzyl)-1H-indole-2-carboxylic acid (2-hydroxy-cyclohexylmethyl)amide

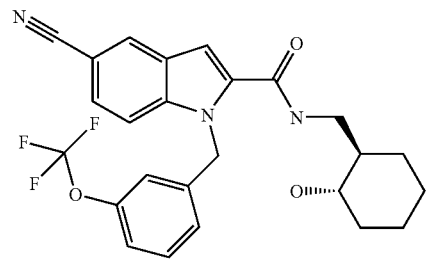

The title compound was prepared using 3-(trifluoromethoxy)benzyl bromide and trans-2-aminomethyl-1-cyclohexanol in a manner similar to that described in Example 18.

$^1$H NMR (400 MHz, MeOD) δ$_H$: 0.80-1.82 (m, 8H), 1.14 (br t, 2H), 3.01-3.09 (m, 1H), 3.14-3.23 (m, 1H), 3.50 (m, 1H), 4.66 (d, 1H, J=5.0), 5.94 (s, 2H), 7.03 (s, 1H), 7.05 (br d, 1H, J=8.2), 7.22 (br d, 1H, J=8.2), 7.40 (t, 1H, J=8.2), 7.60 (dd, 1H, J=8.8, 1.4), 7.80 (d, 1H, J=8.8), 8.30 (d, 1H, J=1.4), 8.66 (tr, 1H, J=5.9);

EIMS: m/z=472.0 [M+H]$^+$.

Example 35 trans-5-Cyano-1-[3-bromobenzyl]-1H-indole-2-carboxylic acid (2-hydroxy-cyclohexylmethyl)amide

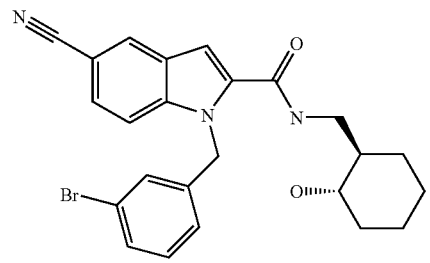

The title compound was prepared using 3-bromobenzyl bromide and trans-2-aminomethyl-1-cyclohexanol in a manner similar to that described in Example 18.

$^1$H NMR (400 MHz, MeOD) δ$_H$: 0.97 (m, 1H), 1.23 (m, 3H), 1.42 (m, 1H), 1.66 (m, 3H), 1.90 (m, 1H), 3.03 (m, 1H), 3.34-3.40 (dd, 1H, J=13.6, 4.0), 3.48-3.55 (dd, 1H, J=13.6, 6.6), 5.80-5.91 (dd, 2H, J=24.4, 16.4), 6.99 (d, 1H, J=8.3), 6.99 (d, 1H, J=8.3), 7.15 (m, 1H), 7.15 (m, 1H), 7.19 (s, 1H), 7.36 (d, 1H, J=7.8), 7.54 (dd, 1H, J=8.6, 1.5), 7.64 (d, 1H, J=8.6), 8.13 (m, 1H);

EIMS: m/z=466.2 [M−H]$^-$.

Example 36

5-Cyano-1-(3,5-dichlorobenzyl)-1H-indole-2-carboxylic acid (3-hydroxy-2,2-dimethylpropyl)amide

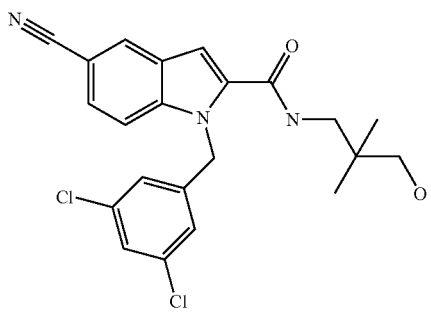

3,5-Dichlorobenzyl bromide, prepared from 3,5-dichlorobenzyl alcohol in a manner similar to that described in Example 11, was used to prepare the title compound in a manner similar to that described in Example 18.

$^1$H NMR (400 MHz, MeOD) $\delta_H$: 0.88 (s, 6H), 3.19 (s, 2H), 3.24 (s, 2H), 5.85 (s, 2H), 6.97 (m, 2H), 7.25 (br s, 1H), 7.29 (t, 1H, J=1.9), 7.56 (dd, 1H, J=8.7, 1.9), 7.63 (d, 1H, J=8.7), 8.15 (br s, 1H);

EIMS: m/z=412.1, 414.1 [M−OH]$^+$.

Example 37

5-Cyano-1-(5-chloro-2-methoxybenzyl)-1H-indole-2-carboxylic acid (3-hydroxy-2,2-dimethylpropyl) amide

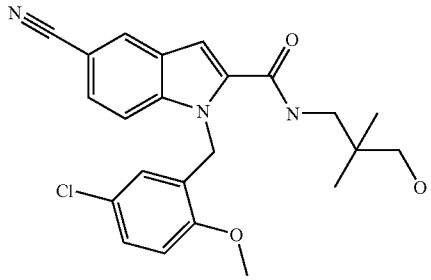

5-Chloro-2-methoxybenzyl bromide, prepared from 5-chloro-2-methoxybenzyl alcohol in a manner similar to that described in Example 11, was used to prepare the title compound in a manner similar to that described in Example 18.

$^1$H NMR (400 MHz, MeOD) $\delta_H$: 0.87 (s, 6H), 3.14 (s, 2H), 3.22 (s, 2H), 3.84 (s, 3H), 5.80 (s, 2H), 6.41 (d, 1H, J=2.8), 6.94 (d, 1H, J=8.8), 7.18 (dd, 1H J=8.8, 2.5), 7.19 (s, 1H), 7.52 (dd, 2H, J=8.8, 1.5), 7.57 (d, 1H, J=8.8), 8.12 (br s, 1H);

EIMS: m/z=426.0 [M+H]$^+$.

Example 38

5-Cyano-1-(5-bromo-2-fluorobenzyl)-1H-indole-2-carboxylic acid (3-hydroxy-2,2-dimethylpropyl) amide

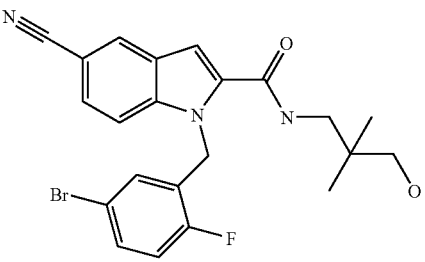

5-Bromo-2-fluorobenzyl bromide, prepared from 5-bromo-2-fluorobenzyl alcohol in a manner similar to that described in Example 11, was used to prepare the title compound in a manner similar to that described in Example 18.

$^1$H NMR (400 MHz, CDCl$_3$) $\delta_H$: 0.95 (s, 6H), 3.16-3.22 (m, 1H), 3.26 (d, 2H, J=5.8), 3.34 (d, 2H, J=6.5), 5.87 (s, 2H), 6.86 (br t, 1H, J=6.5), 6.90-6.94 (m, 1H), 6.97 (t, 1H, J=8.8), 7.02 (s, 1H), 7.31-7.37 (m, 1H), 7.42 (d, 1H, J=8.7), 7.54 (d, 1H, J=8.7), 8.05 (br s, 1H);

EIMS: m/z=458.3, 460.3 [M+H]$^+$.

Example 39

5-Cyano-1-(5-bromo-2-methoxybenzyl)-1H-indole-2-carboxylic acid (3-hydroxy-2,2-dimethylpropyl) amide

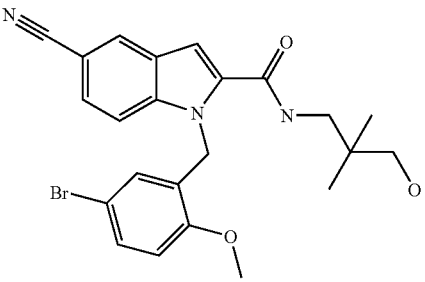

5-Bromo-2-methoxybenzyl bromide, prepared from 5-bromo-2-methoxybenzyl alcohol in a manner similar to that described in Example 11, was used to prepare the title compound in a manner similar to that described in Example 18.

$^1$H NMR (400 MHz, CDCl$_3$) $\delta_H$: 0.90 (s, 6H), 3.12 (m, 2H), 3.15 (m, 1H), 3.29 (d, 2H, J=6.4), 3.86 (s, 3H), 5.78 (s, 2H), 6.55 (d, 1H, J=2.1), 6.73 (br t, 1H, J=6.4), 6.76 (d, 1H, J=8.7), 7.00 (s, 1H), 7.30 (dd, 1H, J=6.5, 2.1), 7.40 (d, 1H, J=8.6), 7.49 (dd, 1H, J=8.6, 1.3), 8.03 (br s, 1H);

EIMS: m/z=470.3, 472.3 [M+H]$^+$.

Example 40

5-Cyano-1-(2,3-dimethoxy-5-bromobenzyl)-1H-indole-2-carboxylic acid (3-hydroxy-2,2-dimethylpropyl)amide

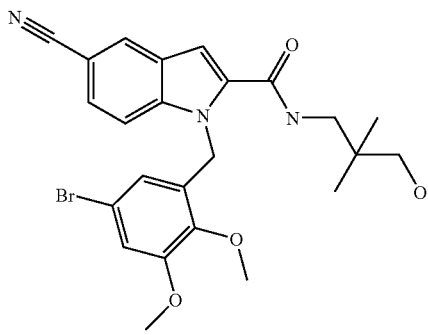

2,3-Dimethoxy-5-bromobenzyl bromide, prepared from 5-bromo-2,3-dimethoxybenzoic acid in a manner similar to that described in Example 11, was used to prepare the title compound in a manner similar to that described in Example 18.

$^1$H NMR (400 MHz, CDCl$_3$) $\delta_H$: 0.93 (s, 6H), 3.15 (s, 2H), 3.30 (d, 2H, J=6.5), 3.85 (s, 3H), 3.86 (s, 3H), 5.83 (s, 2H), 6.30 (d, 1H, J=2.2), 6.80 (t, 1H, J=6.5), 6.91 (d, 1H, J=2.2), 7.01 (s, 1H), 7.40 (d, 1H, J=8.6), 7.48 (dd, 1H, J=8.6, 1.4), 8.02 (br s, 1H);

EIMS: m/z=500.1, 502.1 [M+H]$^+$.

Example 41

5-Cyano-1-(5-tert-butyl-2-methoxybenzyl)-1H-indole-2-carboxylic acid (3-hydroxy-2,2-dimethylpropyl)amide

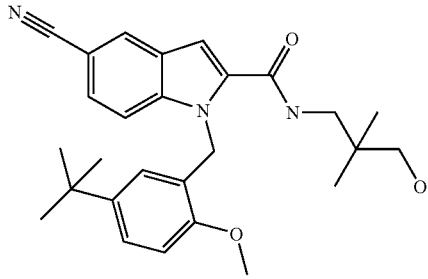

5-tert-Butyl-2-methoxybenzyl bromide, prepared from 5-tert-butyl-2-methoxybenzoic acid in a manner similar to that described in Example 11, was used to prepare the title compound in a manner similar to that described in Example 18.

$^1$H NMR (400 MHz, CDCl$_3$) $\delta_H$: 0.90 (s, 6H), 1.08 (s, 9H), 3.10 (d, 2H, J=6.3), 3.27 (d, 2H, J=6.5), 3.44 (t, 1H, J=6.3), 3.82 (s, 3H), 5.81 (s, 2H), 6.57 (d, 1H, J=2.4), 6.67 (br t, 1H, J=6.5), 6.79 (d, 1H, J=8.5), 6.98 (s, 1H), 7.19 (dd, 1H, J=8.5, 2.4), 7.46 (dd, 1H, J=8.8, 1.5) 7.49 (d, 2H, J=8.8), 8.00 (br s, 1H);

EIMS: m/z=448.3 [M+H]$^+$.

Example 42

5-Cyano-1-(2-methoxy-5-methylbenzyl)-1H-indole-2-carboxylic acid (3-hydroxy-2,2-dimethylpropyl)amide

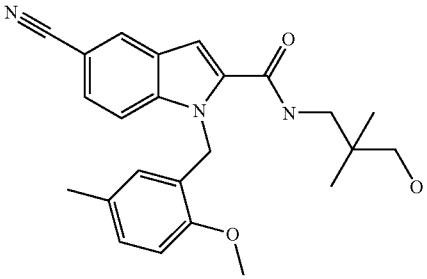

2-Methoxy-5-methylbenzyl bromide, prepared from 2-methoxy-5-methylbenzoic acid in a manner similar to that described in Example 11, was used to prepare the title compound in a manner similar to that described in Example 18.

$^1$H NMR (400 MHz, CDCl$_3$) $\delta_H$: 0.90 (s, 6H), 2.09 (s, 3H), 3.13 (d, 2H, J=6.6), 3.25-3.32 (m, 3H, J=6.5), 3.81 (s, 3H), 5.77 (s, 2H), 6.38 (d, 1H, J=1.8), 6.65 (br t, 1H, J=6.6), 6.76 (d, 1H, J=8.5), 6.96-7.01 (m, 2H), 7.45-7.46 (m, 2H), 8.03 (t, 1H, J=1.3);

EIMS: m/z=406.5 [M+H]$^+$.

Example 43

5-Cyano-1-[3-(2-methoxyethoxy)benzyl]-1H-indole-2-carboxylic acid (3-hydroxy-2,2-dimethylpropyl)amide

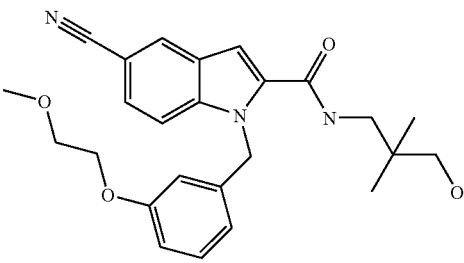

3-Hydroxybenzyl alcohol (3.76 g, 30 mmol), 2-bromoethylmethyl ether (8.0 ml, 85 mmol) and cesium carbonate (14.7 g, 45 mmol) were heated at 60° C. for 3 h. The reaction was diluted with water, extracted (3×) with ethyl acetate and dried over sodium sulfate. The solution was filtered, concentrated and purified by silica chromatography (DCM followed by DCM/MeOH 19:1, then 9:1) to yield [3-(2-methoxyethoxy)phenyl]methanol as an orange oil (3.92 g, 72%).

1-Bromomethyl-3-(2-methoxyethoxy)benzene, prepared from [3-(2-methoxy-ethoxy)phenyl]methanol in a manner similar to that described in Example 11, was used to prepare the title compound in a manner similar to that described in Example 18.

$^1$H NMR (400 MHz, CDCl$_3$) $\delta_H$: 0.89 (s, 6H), 3.15 (d, 2H, J=6.8), 3.27 (d, 2H, J=6.8), 3.33 (t, 1H, J=6.8), 3.40 (s, 3H), 3.66-3.70 (m, 2H), 3.99-4.03 (m, 2H), 5.78 (s, 2H), 6.55 (br s, 1H), 6.65 (d, 1H, J=7.8), 6.75-6.78 (m, 2H), 6.97 (s, 1H), 7.17 (t, 1H, J=7.9), 7.41 (d, 1H, J=8.8), 7.48 (dd, 1H, J=8.8, 1.2), 8.00 (br s, 1H);
EIMS: m/z=436.5 [M+H]$^+$.

Example 44

5-Cyano-1-(3-isopropoxybenzyl)-1H-indole-2-carboxylic acid (3-hydroxy-2,2-dimethylpropyl)amide

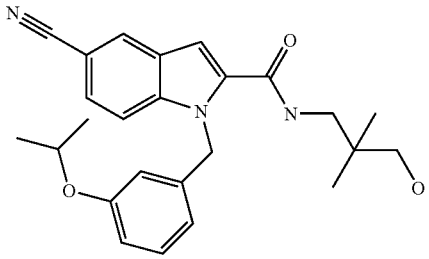

A mixture of 3-hydroxybenzyl alcohol (2.00 g, 0.014 mol), 2-iodopropane (2.4 ml, 8.29 mmol), cesium carbonate (8.00 g, 0.0246 mol) in DMF (10 ml) was heated at 85° C. for 8 h. The reaction was diluted with water (100 ml) and extracted with DCM (30 ml) and this was washed with water (2×30 ml). The product was chromatographed on silica using DCM:methanol (19:1) to afford 3-isopropoxybenzyl alcohol (1.70 g, 73%) as an orange liquid.

3-Isopropoxybenzyl bromide, prepared from 3-isopropoxybenzyl alcohol in a manner similar to that described in Example 11, was used to prepare the title compound in a manner similar to that described in Example 18.

$^1$H NMR (400 MHz, MeOD) δ$_H$: 0.87 (s, 6H), 1.19 (d, 6H, J=6.0), 3.17 (s, 2H), 3.23 (s, 2H), 4.43 (sept, 1H, J=6.0), 5.81 (s, 2H), 6.48 (s, 1H), 6.58 (d, 1H, J=8.2), 6.72 (d, 1H, J=8.2), 7.12 (t, 1H, J=8.2), 7.18 (s, 1H), 7.51 (dd, 1H, J=8.6, 1.5), 7.62 (d, 1H, J=8.6), 8.12 (br s, 1H);
EIMS: m/z=420.4 [M+H]$^+$.

Example 45

5-Cyano-1-(3-oxazol-5-yl-benzyl)-1H-indole-2-carboxylic acid (3-hydroxy-2,2-dimethylpropyl)amide

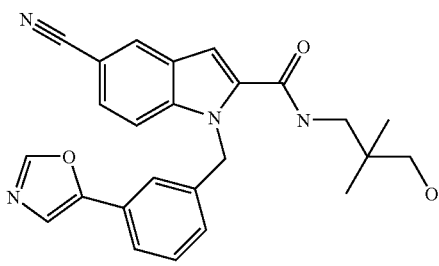

To a solution of isophthalaldehyde (1.77 g, 13.0 mmol) in EtOH (30 ml) at 0° C., was added sodium borohydride (135 mg, 3.5 mmol). The reaction was stirred at 0° C. for 1 h. The solvent was evaporated and the residue purified by silica chromatography using DCM followed by DCM:MeOH (19:1) to yield 3-hydroxymethyl-benzaldehyde (1.14 g, 64%) as a yellow oil.

3-Hydroxymethyl-benzaldehyde (1.14 g, 8.35 mmol), tosylmethyl isocyanide (2.47 g, 12.5 mmol) and potassium carbonate (1.75 g, 12.5 mmol) in methanol (25 ml) were refluxed at 85° C. for 1 h. The reaction was concentrated, residue dissolved in DCM/water and separated using a hydrophobic filter tube. The organic phase was concentrated and purified by silica chromatography using DCM followed by DCM:MeOH (19:1) to yield (3-oxazol-5-yl-phenyl)methanol (1.32 g, 90%) as an orange oil.

5-(3-bromomethylphenyl)oxazole, prepared from 3-oxazol-5-yl-phenyl)methanol in a manner similar to that described in Example 11, was used to prepare the title compound in a manner similar to that described in Example 18.

$^1$H NMR (400 MHz, CDCl$_3$) δ$_H$: 0.89 (s, 6H), 3.15-3.25 (m, 3H), 3.30 (d, 2H, J=6.0), 5.87 (s, 2H), 6.81 (br t, 1H, J=6.0), 6.99 (d, 1H, J=7.9), 7.02 (s, 1H), 7.29 (s, 1H), 7.32 (t, 1H, J=7.9), 7.39 (br s, 1H), 7.45 (d, 1H, J=8.4), 7.48-7.55 (m, 2H), 7.87 (s, 1H), 8.03 (br s, 1H);
EIMS: m/z=429.3 [M+H]$^+$.

Example 46

5-Cyano-1-(3-imidazol-1-yl-benzyl)-1H-indole-2-carboxylic acid (3-hydroxy-2,2-dimethylpropyl)amide

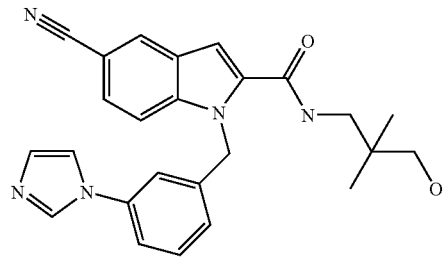

3-Iodobenzylalcohol (5.17 g, 21.0 mmol), imidazole (1.73 g, 25.2 mmol), potassium carbonate (3.78 g, 27.3 mmol), copper (0) powder (275 mg, 4.33 mmol) and potassium fluoride (260 mg, 4.44 mmol) in DMF (30 ml) were refluxed at 175° C. for 6 h. The reaction was filtered, the solid washed with DCM and washing and filtrate concentrated. Purification by silica chromatography using DCM followed by DCM:MeOH (15:1 then 10:1) yielded (3-imidazol-1-yl-phenyl)-methanol as an orange oil (3.17 g, 72%).

Thionyl chloride (4.0 ml, 54.0 mmol) was added to a solution of (3-imidazol-1-yl-phenyl)-methanol (3.17 g, 17.0 mmol) in DMF (50 ml) and the reaction stirred at room temperature for 40 h. The solvent was evaporated, the residue diluted with DCM and washed with water, neutralised with aqueous sodium bicarbonate (pH 9-10) and then extracted with DCM (3×). The organic phase was dried over sodium sulfate, filtered and concentrated to give 1-(3-chloromethylphenyl)-1H-imidazole as an orange oil (5.3 g, crude contaminated with DMF).

The title compound was prepared using the crude 1-(3-chloromethylphenyl)-1H-imidazole in a manner similar to that described in Example 18.

$^1$H NMR (400 MHz, CDCl$_3$) δ$_H$: 0.90 (s, 6H), 3.18 (s, 2H), 3.30 (d, 2H, J=6.4), 5.89 (s, 2H), 6.97 (br t, 1H, J=6.4), 7.00-7.05 (m, 2H), 7.09 (br s, 1H), 7.15 (br s, 1H), 7.20 (br s, 1H), 7.22-7.27 (m, 1H), 7.38 (t, 1H, J=7.8), 7.43 (d, 1H, J=8.9), 7.52 (dd, 1H, J=8.9, 1.4), 7.75 (br s, 1H), 8.04 (br s, 1H);
EIMS: m/z=428.3 [M+H]$^+$.

Example 47 trans-5-Cyano-1-[3-(4-methyl-piperazin-1-yl)-benzyl]-1H-indole-2-carboxylic acid (2-hydroxy-cyclohexylmethyl)amide

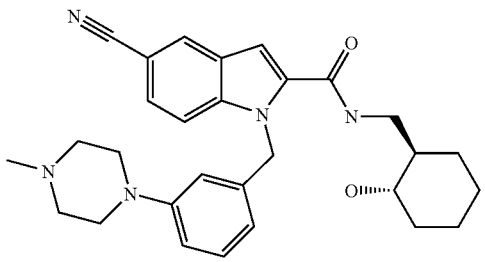

A mixture of 5-cyano-1-[3-bromobenzyl]-1H-indole-2-carboxylic acid (2-hydroxy-cyclohexylmethyl)amide (prepared using 3-bromobenzyl bromide and 3-amino-2,2-dimethyl-1-propanol in a manner similar to that described in Example 35) (0.250 g, 0.54 mmol), tris(dibenzylidineacetone)dipalladium (125 mg, 0.014 mmol), 2-(dicyclohexylphosphine) biphenyl (9.6 mg, 0.027 mmol), potassium phosphate (1.44 g, 0.82 mmol) and N-methylpiperazine (64 mg, 0.64 mmol) in 1,2-dimethoxyethane (3 ml) were heated in a sealed Reactavial at 100° C. under nitrogen for 30 h. After cooling to ambient temperature, the mixture was filtered through dicalite and the resulting filtrate evaporated to dryness. Purification was fulfilled by chromatography on silica using DCM:methanol (19:1) as eluent, affording the title compound (0.021 g, 8%).

$^1$H NMR (400 MHz, MeOD) $\delta_H$: 0.97 (m, 1H), 1.20 (m, 3H), 1.42 (m, 1H), 1.65 (m, 3H), 1.89 (m, 1H), 2.31 (s, 3H), 2.55 (t, 4H, J=5.0), 3.03 (m, 1H), 3.08 (t, 4H, J=5.0), 3.34 (d, 1H, J=4.0), 3.37 (d, 1H, J=4.2), 3.53 (q, 1H, J=6.5), 5.80 (dd, 2H, J=23.6, 16.0), 6.47 (d, 1H, J=7.5), 6.59 (m, 1H), 6.81 (dd, 1H, J=8.0), 7.14 (s, 1H), 7.46 (dd, 1H, J=8.8, 1.8), 7.64 (d, 1H, J=8.5), 8.10 (m, 1H);

EIMS: m/z 486.2 [M+H]$^+$.

Example 48

(S)-(+)-5-Cyano-1-(3-trifluoromethoxybenzyl)-1H-indole-2-carboxylic acid (1-hydroxymethyl-2-methylpropyl)amide

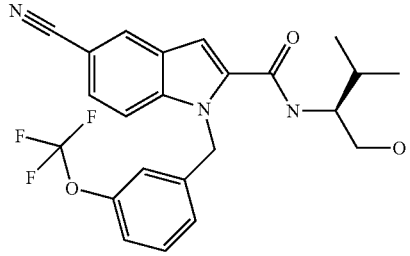

The title compound was prepared using 5-cyano-1-(3-trifluoromethoxybenzyl)-1H-indole-2-carboxylic acid [prepared from 3-(trifluoromethoxy)benzyl bromide and ethyl 5-cyanoindole-2-carboxylate] and (S)-(+)-2-amino-3-methyl-1-butanol in a manner similar to that described in Example 11.

$^1$H NMR (400 MHz, MeOD) $\delta_H$: 0.89 (d, 3H, J=7.0), 0.95 (d, 3H, J=6.8), 1.93 (oct, 1H, J=6.8, 7.0), 3.63 (dd, 1H, J=11.4, 6.5), 3.69 (dd, 1H, J=11.4, 4.4), 3.85 (ddd, 1H, J=11.4, 6.8, 4.5), 5.85, 5.93 (ABq, 2H, J=16.3), 6.96 (br s, 1H), 7.05 (br d, 1H, J=7.9), 7.11 (br d, 1H, J=7.9), 7.28 (s, 1H), 7.34 (t, 1H, J=7.9), 7.52 (dd, 1H, J=8.8, 1.5), 7.62 (d, 1H, J=8.8), 8.14 (br s, 1H);

EIMS: m/z=446.0 [M+H]$^+$.

Example 49

5-Cyano-1-(3-trifluoromethoxybenzyl)-1H-indole-2-carboxylic acid (tetrahydro-furan-2-yl)-amide

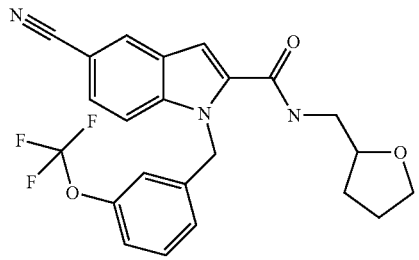

The title compound was prepared using 5-cyano-1-(3-trifluoromethoxy-benzyl)-1H-indole-2-carboxylic acid [prepared from 3-(trifluoromethoxy)benzyl bromide and ethyl 5-cyanoindole-2-carboxylate] and tetrahydrofurfurylamine in a manner similar to that described in Example 11.

$^1$H NMR (400 MHz, MeOD) $\delta_H$: 1.52-1.64 (m, 1H), 1.81-2.01 (m, 3H), 3.34-3.48 (m, 2H), 3.70-3.77 (m, 1H), 3.82-3.89 (m, 1H), 3.99-4.07 (m, 1H), 5.90 (s, 2H), 6.91 (br s, 1H), 7.03 (br d, 1H, J=8.0), 7.12 (d, 1H, J=8.0), 7.24 (s, 1H), 7.34 (t, 1H, J=8.0), 7.52 (dd, 1H, J=8.6, 1.5), 7.62 (d, 1H, J=8.6), 8.13 (br s, 1H);

EIMS: m/z 444.0 [M+H]$^+$.

Example 50

R-(+)-5-Cyano-1-(3-trifluoromethoxybenzyl)-1H-indole-2-carboxylic acid (tetrahydro-furan-3-yl)-amide

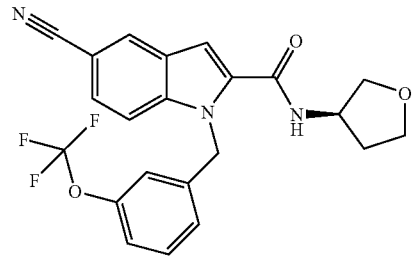

The title compound was prepared using 5-cyano-1-(3-trifluoromethoxybenzyl)-1H-indole-2-carboxylic acid [prepared from 3-(trifluoromethoxy)benzyl bromide and ethyl 5-cyanoindole-2-carboxylate] and R-(+)-3-aminotetrahydrofuran toluene-4-sulfonate in a manner similar to that described in Example 11.

¹H NMR (400 MHz, d6-DMSO) δ_H: 1.82-1.94 (m, 1H), 2.07-2.20 (m, 1H), 3.49-3.59 (m, 1H), 3.66-3.75 (m, 1H), 3.76-3.89 (m, 2H), 4.35-4.49 (m, 1H), 5.92 (s, 2H), 7.02-7.12 (m, 2H), 7.22 (d, 1H, J=8.2), 7.37 (s, 1H), 7.40 (t, 1H, J=8.2), 7.60 (dd, 1H, J=8.5, 1.5), 7.78 (d, 1H, J=8.5), 8.31 (d, 1H, J=1.5), 8.80 (d, 1H, J=6.5);
EIMS: m/z 400.0.

Example 51 cis-5-Cyano-1-(3-trifluoromethoxybenzyl)-1H-indole-2-carboxylic acid (2-hydroxymethylcyclohexyl)-amide

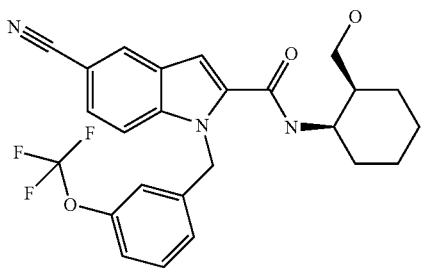

The title compound was prepared using 5-cyano-1-(3-trifluoromethoxy-benzyl)-1H-indole-2-carboxylic acid [prepared from 3-(trifluoromethoxy)benzyl bromide and ethyl 5-cyanoindole-2-carboxylate] and cis-2-hydroxymethyl-1-cyclohexylamine in a manner similar to that described in Example 11.

¹H NMR (400 MHz, MeOD) δ_H: 1.33-1.69 (m, 7H), 1.71-1.84 (m, 1H), 1.86-1.96 (m, 1H), 3.43 (dd, 1H, J=11.2, 6.2), 3.51 (dd, 1H, J=8.2, 11.2), 4.26-4.31 (m, 1H), 5.86 (s, 2H), 6.97 (br s, 1H), 7.05 (br d, 1H, J=7.7), 7.12 (br d, 1H, J=7.7), 7.20 (s, 1H), 7.35 (t, 1H, J=7.7), 7.52 (dd, 1H, J=8.8, 1.8), 7.63 (d, 1H, J=8.8), 8.13 (br s, 1H);
EIMS: m/z=472.3 [M+H]⁺.

Example 52

5-Cyano-1-(3-trifluoromethoxybenzyl)-1H-indole-2-carboxylic acid (1-cyclopropyl-3-hydroxypropyl)amide

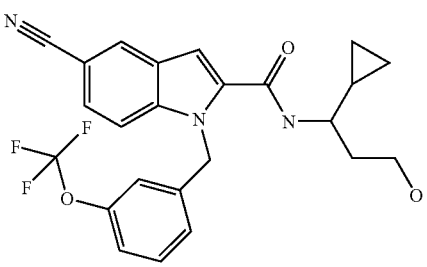

The title compound was prepared using 5-cyano-1-(3-trifluoromethoxybenzyl)-1H-indole-2-carboxylic acid [prepared from 3-(trifluoromethoxy)benzyl bromide and ethyl 5-cyanoindole-2-carboxylate] and 3-amino-3-cyclopropyl-propan-1-ol in a manner similar to that described in Example 11.

¹H NMR (400 MHz, CDCl₃) δ_H: 0.25-0.40 (m, 2H), 0.48-0.56 (m, 1H), 0.57-0.65 (m, 1H), 0.90-1.00 (m, 1H), 1.50-1.65 (m, 1H), 1.98-2.10 (m, 1H), 2.83 (br, 1H), 3.50-3.60 (m, 2H), 3.60-3.70 (m, 1H), 5.83 (s, 2H), 6.49 (d, 1H, J=8.0), 6.84 (s, 1H), 7.00 (d, 1H, J=7.9), 7.03 (s, 1H), 7.09 (d, 1H, J=7.9), 7.30 (t, 1H, J=7.9), 7.40 (d, 1H, J=8.7), 7.50 (dd, 1H, J=8.7, 1.4), 8.03 (br s, 1H);
EIMS: m/z=458.1 [M+H]⁺.

Example 53

5-Cyano-1-(3-trifluoromethoxybenzyl)-1H-indole-2-carboxylic acid (3-hydroxybutyl)amide

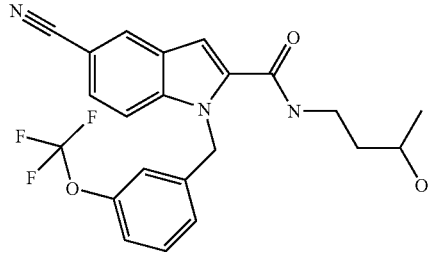

The title compound was prepared using 5-cyano-1-(3-trifluoromethoxy-benzyl)-1H-indole-2-carboxylic acid [prepared from 3-(trifluoromethoxy)benzyl bromide and ethyl 5-cyanoindole-2-carboxylate] and 4-amino-2-butanol in a manner similar to that described in Example 11.

¹H NMR (400 MHz, CDCl₃) δ_H: 1.22 (d, 3H, J=6.3), 1.55-1.65 (m, 1H), 1.68-1.80 (m, 1H), 2.39 (br s, 1H), 3.25-3.40 (m, 1H), 3.75-3.90 (m, 2H), 5.84, 5.87 (ABq, 2H, J=16.3), 6.87 (br s, 1H), 6.90-7.02 (m, 3H), 7.08 (br d, 1H, J=8.0), 7.29 (t, 1H, J=8.0), 7.37 (d, 1H, J=8.8), 7.50 (dd, 1H, J=8.8, 1.2), 8.02 (br s, 1H);
EIMS: m/z=432.1 [M+H]⁺.

Example 54 trans-5-Cyano-1-(3-trifluoromethoxybenzyl)-1H-indole-2-carboxylic acid (2-hydroxy-cyclopentyl)amide

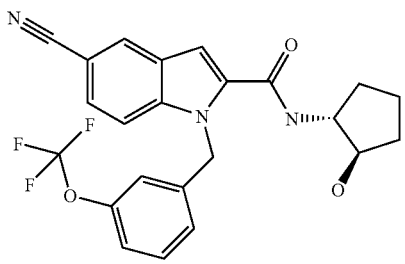

The title compound was prepared using 5-cyano-1-(3-trifluoromethoxybenzyl)-1H-indole-2-carboxylic acid [prepared from 3-(trifluoromethoxy)benzyl bromide and ethyl 5-cyanoindole-2-carboxylate] and trans-2-aminocyclopentanol hydrochloride in a manner similar to that described in Example 11.

¹H NMR (400 MHz, CDCl₃) δ_H: 1.40-1.50 (m, 1H), 1.65-1.80 (m, 2H), 1.80-1.90 (m, 1H), 2.00-2.10 (m, 1H), 2.20-

2.30 (m, 1H), 3.77 (br s, 1H), 3.95-1.05 (m, 2H), 5.83 (s, 2H), 6.27 (br s, 1H), 6.88 (br s, 1H), 6.95-7.05 (m, 2H), 7.09 (br d, 1H, J=7.8), 7.30 (t, 1H, J=7.8), 7.40 (d, 1H, J=8.7), 7.50 (dd, 1H, J=8.7, J=1.3), 8.02 (br s, 1H);

EIMS: m/z=444.1 [M+H]⁺.

Example 55

5-Cyano-1-(3-trifluoromethoxybenzyl)-1H-indole-2-carboxylic acid (1-hydroxymethylpropyl)amide

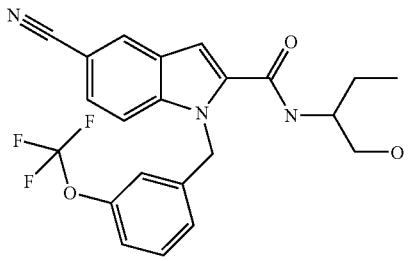

The title compound was prepared using 5-cyano-1-(3-trifluoromethoxybenzyl)-1H-indole-2-carboxylic acid [prepared from 3-(trifluoromethoxy)benzyl bromide and ethyl 5-cyanoindole-2-carboxylate] and 2-amino-1-butanol in a manner similar to that described in Example 11.

¹H NMR (400 MHz, MeOD) δ$_H$: 0.90 (t, 3H, J=7.4), 1.43-1.56 (m, 1H), 1.64-1.76 (m, 1H), 3.58 (d, 2H, J=5.5), 3.91-3.99 (m, 1H), 4.49 (br s, 1H), 5.86, 5.93 (ABq, 2H, J=16.4), 6.96 (br s, 1H), 7.05 (br d, 1H, J=8.0), 7.12 (br d, 1H, J=8.0), 7.26 (s, 1H), 7.34 (t, 1H, J=8.0), 7.53 (dd, 1H, J=8.6, 1.5), 7.62 (d, 1H, J=8.6), 8.13 (br s, 1H);

EIMS: m/z=432.4 (M+H)⁺.

Example 56

5-Cyano-1-(3-trifluoromethoxybenzyl)-1H-indole-2-carboxylic acid (1-hydroxymethyl-3-methylsulfanyl-propyl)amide

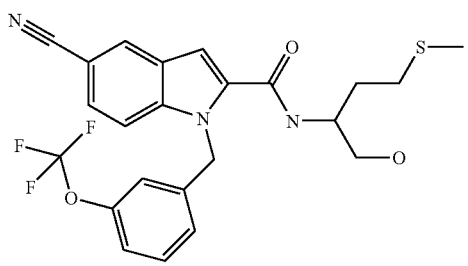

The title compound was prepared using 5-cyano-1-(3-trifluoromethoxybenzyl)-1H-indole-2-carboxylic acid [prepared from 3-(trifluoromethoxy)benzyl bromide and ethyl 5-cyanoindole-2-carboxylate] and L-(−)-methioninol in a manner similar to that described in Example 11.

¹H NMR (400 MHz, MeOD) δ$_H$: 1.72-1.85 (m, 1H), 1.88-2.01 (m, 1H), 2.04 (s, 3H), 2.40-2.52 (m, 2H), 3.53-3.63 (m, 2H), 4.12-4.22 (m, 1H), 5.86, 5.93 (ABq, 2H, J=16.2), 6.94 (s, 1H), 7.04 (br d, 1H, J=7.9), 7.12 (d, 1H, J=7.9), 7.27 (s, 1H), 7.34 (t, 1H, J=7.9), 7.49-7.55 (m, 1H), 7.61 (d, 1H, J=8.5), 8.13 (br s, 1H);

EIMS: m/z=478.0 (M+H)⁺.

Example 57

5-Cyano-1-(3-trifluoromethoxybenzyl)-1H-indole-2-carboxylic acid (3-hydroxy-propyl)amide

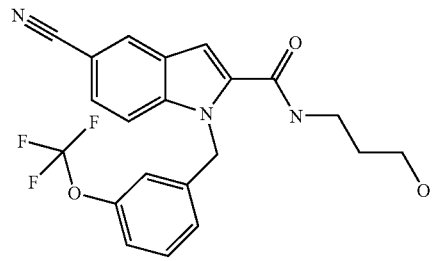

The title compound was prepared using 5-cyano-1-(3-trifluoromethoxybenzyl)-1H-indole-2-carboxylic acid [prepared from 3-(trifluoromethoxy)benzyl bromide and ethyl 5-cyanoindole-2-carboxylate] and 3-amino-1-propanol in a manner similar to that described in Example 11.

¹H NMR (400 MHz, MeOD) δ$_H$: 1.74-1.82 (quint, 2H, J=6.5), 3.43 (t, 2H, J=6.5), 3.59 (t, 2H, J=6.5), 5.90 (s, 2H), 6.95 (br s, 1H), 7.04 (br d, 1H, J=8.0), 7.11 (d, 1H, J=8.0), 7.20 (s, 1H), 7.34 (dd, 1H, J=8.0), 7.53 (dd, 1H, J=8.5, 1.5), 7.61 (d, 1H, J=8.7), 8.13 (br s, 1H);

EIMS: m/z=418.0 (M+H)⁺.

Example 58

5-Cyano-1-(3-trifluoromethoxybenzyl)-1H-indole-2-carboxylic acid (2-hydroxy-butyl)amide

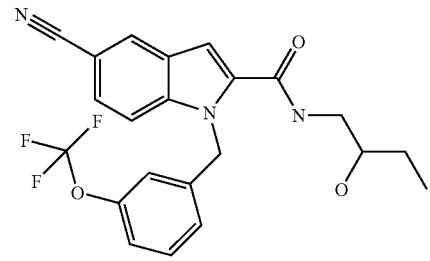

The title compound was prepared using 5-cyano-1-(3-trifluoromethoxybenzyl)-1H-indole-2-carboxylic acid [prepared from 3-(trifluoromethoxy)benzyl bromide and ethyl 5-cyanoindole-2-carboxylate] and 1-amino-2-butanol in a manner similar to that described in Example 11.

¹H NMR (400 MHz, MeOD) δ$_H$: 0.92-1.00 (m, 3H), 1.35-1.45 (m, 1H), 1.45-1.57 (m, 1H), 3.26-3.34 (m, 1H), 3.39-3.47 (m, 1H), 3.60-3.68 (m, 1H), 5.91 (s, 2H), 6.97 (s, 1H), 7.04 (d, 1H, J=7.8), 7.13 (d, 1H, J=8.3), 7.23-7.28 (m, 1H), 7.30-7.38 (m, 1H), 7.50-7.56 (m, 1H), 7.58-7.63 (m, 1H), 8.11-8.15 (m, 1H);

EIMS: m/z=432.3 (M+H)⁺.

Example 59

5-Cyano-1-(3-trifluoromethoxybenzyl)-1H-indole-2-carboxylic acid [2-hydroxy-1-(tetrahydropyran-4-yl)ethyl]amide

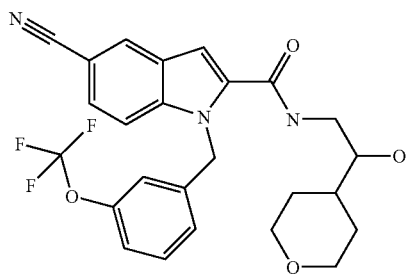

The title compound was prepared using 5-cyano-1-(3-trifluoromethoxybenzyl)-1H-indole-2-carboxylic acid [prepared from 3-(trifluoromethoxy)benzyl bromide and ethyl 5-cyanoindole-2-carboxylate] and 2-amino-2-(tetrahydropyran-4-yl)ethanol in a manner similar to that described in Example 11.

$^1$H NMR (400 MHz, MeOD) $\delta_H$: 1.20-1.40 (m, 2H), 1.47 (d, 1H, J=12.8), 1.66 (d, 1H, J=12.8), 1.80-1.95 (m, 1H), 3.30-3.40 (m, 2H), 3.60-3.75 (m, 2H), 3.80-4.00 (m, 3H), 5.85, 5.94 (ABq, 2H, J=16.6), 6.92 (br s, 1H), 7.03 (br d, 1H, J=8.0), 7.12 (br d, 1H, J=8.0), 7.28 (s, 1H), 7.34 (t, 1H, J=8.0), 7.53 (d, 1H, J=8.7), 7.63 (d, 1H, J=8.7), 8.14 (br s, 1H);

EIMS: m/z=488.1 [M+H]$^+$.

Example 60

5-Cyano-1-(3-trifluoromethoxybenzyl)-1H-indole-2-carboxylic acid (1-hydroxy-cyclohexylmethyl)amide

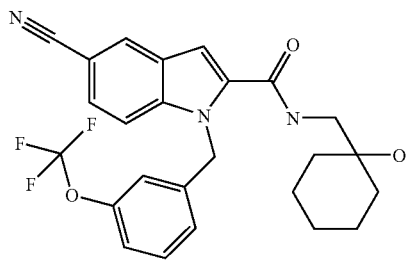

The title compound was prepared using 5-cyano-1-(3-trifluoromethoxybenzyl)-1H-indole-2-carboxylic acid [prepared from 3-(trifluoromethoxy)benzyl bromide and ethyl 5-cyanoindole-2-carboxylate] and 1-aminomethyl-1-cyclohexanol hydrochloride in a manner similar to that described in Example 11.

$^1$H NMR (400 MHz, MeOD) $\delta_H$: 1.20-1.68 (m, 10H), 3.35 (s, 2H), 5.91 (s, 2H), 6.94 (br s, 1H), 7.02 (br d, 1H, J=8.2), 7.12 (br d, 1H, J=8.2), 7.28 (s, 1H), 7.34 (t, 1H, J=8.2), 7.53 (dd, 1H, J=8.8, 1.5), 7.63 (d, 1H, J=8.8), 8.14 (d, 1H, J=1.5);

EIMS: m/z=472.0 [M+H]$^+$.

Example 61 trans-5-Cyano-1-(3-trifluoromethoxybenzyl)-1H-indole-2-carboxylic acid (4-hydroxy-cyclohexyl)amide

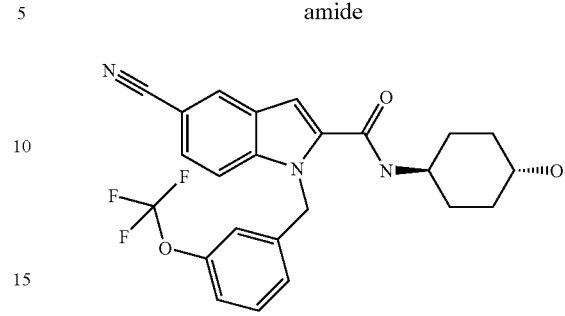

The title compound was prepared using 5-cyano-1-(3-trifluoromethoxybenzyl)-1H-indole-2-carboxylic acid [prepared from 3-(trifluoromethoxy)benzyl bromide and ethyl 5-cyanoindole-2-carboxylate] and trans-4-aminocyclohexanol hydrochloride in a manner similar to that described in Example 11 but using 1,3-diisopropylcarbodiimide instead of 1-(3-dimethylaminopropyl)-3-ethylcarbodiimide.

$^1$H NMR (400 MHz, DMSO-d6) $\delta_H$: 1.13-1.39 (m, 5H), 1.73-1.88 (m, 3H), 3.00-3.09 (m, 1H), 4.53 (d, 1H, J=4.3), 5.47 (br d, 1H, J=7.5), 5.91 (s, 2H), 7.04-7.10 (m, 2H), 7.21 (br d, 1H, J=8.2), 7.27 (s, 1H), 7.39 (t, 1H, J=8.2), 7.58 (dd, 1H, J=8.6, 1.3), 7.78 (d, 1H, J=8.6), 8.27 (d, 1H, J=1.3), 8.52 (d, 1H, J=8.0);

EIMS: m/z=458.2 [M+H]$^+$.

Example 62

5-Cyano-1-(3-trifluoromethoxybenzyl)-1H-indole-2-carboxylic acid (2-methoxyethyl)amide

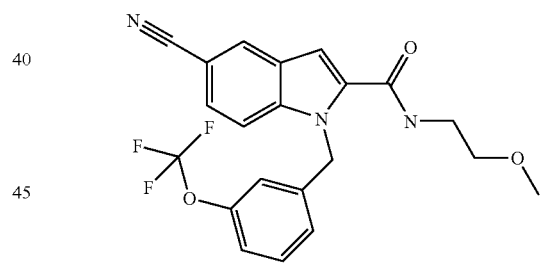

5-Cyano-1-(3-trifluoromethoxybenzyl)-1H-indole-2-carboxylic acid (1.00 g, 2.77 mmol) was suspended in anhydrous DCM (20 ml) and thionyl chloride (0.5 ml, 6.85 mmol) added. The reaction was heated under reflux for 3 h then evaporated to dryness. The residue was dissolved in anhydrous DCM and spit into 4 aliquots, one aliquot was added to a solution of methoxyethylamine (0.075 ml, 1.00 mmol) and triethylamine (0.14 ml, 1.00 mmol) in DCM (5 ml). After stirring for 2 h the reaction was washed with water (2 ml) then evaporated to dryness. Crude product was purified by silica chromatography using DCM as eluent then crystallised from DCM:diethyl ether to provide crystalline title compound.

$^1$H NMR (400 MHz, CDCl$_3$) $\delta_H$: 3.38 (s, 3H), 3.50-3.54 (m, 2H), 3.57-3.63 (m, 2H), 5.85 (s, 2H), 6.56 (br s, 1H), 6.93 (br s, 1H), 6.97 (br d, 1H, J=8.0), 7.01 (s, 1H), 7.08 (br d, 1H, J=8.0), 7.28 (t, 1H, J=8.0), 7.37 (d, 1H, J=8.8), 7.49 (dd, 1H, J=8.8, 1.5), 8.03 (br s, 1H);

EIMS: m/z 418.0 [M+H]$^+$.

Example 63

5-Cyano-1-(3-trifluoromethoxybenzyl)-1H-indole-2-carboxylic acid (3-methoxypropyl)amide

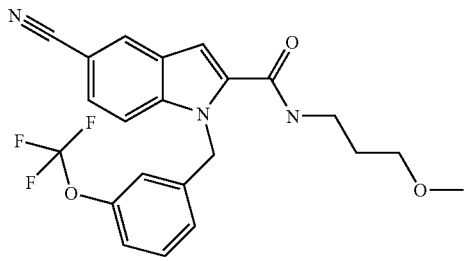

The title compound was prepared using 5-cyano-1-(3-trifluoromethoxybenzyl)-1H-indole-2-carboxylic acid (prepared from 3-(trifluoromethoxy)benzyl bromide and ethyl 5-cyanoindole-2-carboxylate) 2-methoxypropylamine in a manner similar to that described in Example 62.

$^1$H NMR (400 MHz, CDCl$_3$) $\delta_H$: 1.86 (quint, 2H, J=5.8), 3.39 (s, 3H), 3.55 (m, 4H), 5.86 (s, 2H), 6.90-6.94 (m, 2H), 6.98 (d, 1H, J=7.9), 7.01-7.10 (m, 2H), 7.27 (t, 1H, J=7.9), 7.36 (d, 1H, J=8.7), 7.49 (dd, 1H, J=8.7, 1.5), 8.03 (br s, 1H);

EIMS: m/z=446.0 [M+H]$^+$.

Example 64

5-Cyano-1-(2-methyl-5-trifluoromethylbenzyl)-1H-indole-2-carboxylic acid (3-hydroxy-3-methylbutyl)amide

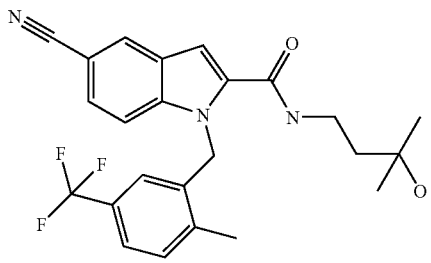

3-Methyl-2-butene-1-amine hydrochloride (2.86 g, 0.02 mmoles) was dissolved in 5% aqueous sulfuric acid (25 ml) and heated to 90° C. for 18 h. The solvent was removed under reduced pressure yielding 4-amino-2-methyl-butan-2-ol sulfate as a yellow oil (4.73 g, 85%).

The title compound was prepared using 5-cyano-1-[2-methyl-5-(trifluoromethyl)]benzyl-1H-indole-2-carboxylic acid [prepared from 2-methyl-5-(trifluoromethyl)benzyl bromide and ethyl 5-cyanoindole-2-carboxylate] and 4-amino-2-methyl-butan-2-ol sulfate in a manner similar to that described in Example 11.

$^1$H NMR (400 MHz, CDCl$_3$) $\delta_H$: 1.30 (s, 6H), 1.56 (s, 1H), 1.72 (t, 2H, J=6.3), 2.47 (s, 3H), 3.50-3.57 (m, 2H), 5.87 (s, 2H), 6.47 (s, 1H), 7.00 (s, 1H), 7.22 (d, 1H, J=8.7), 7.30 (d, 1H, J=7.8), 7.38 (d, 1H, J=7.8), 7.41-7.44 (m, 1H), 7.45 (dd, 2H, J=8.7, 1.5), 8.03-8.05 (m, 1H);

EIMS: m/z 444.3 [M+H]$^+$, 426.0 [M−OH]$^+$.

Example 65

5-Cyano-1-(3-trifluoromethoxybenzyl)-1H-indole-2-carboxylic acid (1-hydroxy-cyclopentylmethyl)amide

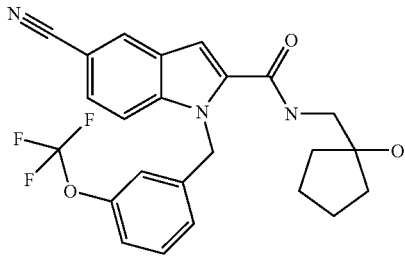

To a cooled mixture of cyclopentanone (1.10 g, 13.0 mmol) and zinc bromide (40 mg, 0.17 mmol) was added dropwise trimethylsilyl cyanide (2.0 ml, 14.7 mmol). The reaction was stirred at room temperature for 30 min. The cyanohydrin solution was then added dropwise to a solution of lithium aluminium hydride (1.67 g, 42 mmol) in ether (30 ml) at a rate sufficient to maintain gentle reflux. This suspension was then refluxed for 1 h, allowed to cool and water (2 ml), 4M aqueous sodium hydroxide (2 ml) followed by water (10 ml) added. The resultant precipitate was filtered through a pad of dicalite, the organic phase separated and dried over potassium hydroxide. The solution was decanted, dried over sodium sulfate, filtered and concentrated. The residue was diluted with diethyl ether and a solution of 2M hydrochloric acid in ether added. The resultant precipitate was collected, washed with ether and dried to yield 1-aminomethyl-cyclopentanol hydrochloride (775 mg, 40%).

The title compound was prepared using 5-cyano-1-(3-trifluoromethoxybenzyl)-1H-indole-2-carboxylic acid [prepared from 3-(trifluoromethoxy)benzyl bromide and ethyl 5-cyanoindole-2-carboxylate] and 1-aminomethyl-cyclopentanol hydrochloride in a manner similar to that described in Example 11.

$^1$H NMR (400 MHz, CDCl$_3$) $\delta_H$: 1.58-1.72 (m, 6H), 1.74 (s, 1H), 1.78-1.88 (m, 2H), 3.53 (d, 2H, J=5.6), 6.67 (br t, 1H, J=5.6), 6.91 (br s, 1H), 6.97 (d, 1H, J=7.8), 7.02 (s, 1H), 7.08 (d, 1H, J=7.8), 7.28 (t, 1H, J=7.8), 7.39 (d, 1H, J=8.8), 7.50 (dd, 1H, J=8.8, 1.6), 8.03 (br s, 1H);

EIMS: m/z=458.4 [M+H]$^+$.

Example 66

5-Cyano-1-(3-trifluoromethoxybenzyl)-1H-indole-2-carboxylic acid (1-hydroxy-cyclobutylmethyl)amide The title compound was prepared using 5-cyano-1-(3-trifluoromethoxybenzyl)-1H-indole-2-carboxylic acid [prepared from 3-(trifluoromethoxy)benzyl bromide and ethyl 5-cyanoindole-2-carboxylate] in a manner similar to that described in Example 11, and 1-aminomethyl-cyclobutanol hydrochloride (prepared from cyclobutanone and trimethylsilyl cyanide) in a manner similar to that described in Example 65.

$^1$H NMR (400 MHz, MeOD) $\delta_H$: 1.49-1.66 (m, 1H), 1.67-1.80 (m, 1H), 1.94-2.12 (m, 4H), 3.53 (s, 2H), 5.89 (s, 2H), 6.97 (br s, 1H), 7.02 (br d, 1H, J=7.8), 7.10 (br d, 1H, J=7.8), 7.26 (s, 1H), 7.32 (t, 1H, J=7.8), 7.49 (dd, 1H, J=8.8, 1.5), 7.58 (d, 1H, J=8.8), 8.09 (br s, 1H);

EIMS: m/z=442.0 [M−H]$^-$.

Example 67

5-Cyano-1-(3-trifluoromethoxybenzyl)-1H-indole-2-carboxylic acid (1-hydroxymethylcyclopropyl)amide

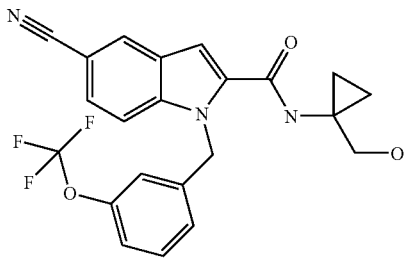

1-Amino-cyclopropanecarboxylic acid ethyl ester hydrochloride (350 mg, 2.11 mmol) was dissolved in anhydrous THF (15 ml) and cooled to 0° C. under argon. A 1.0M solution of lithium aluminium hydride in THF (2.5 ml, 2.50 mmol) was added dropwise and the reaction allowed to warm to room temperature and stirred for 17 h. The reaction was quenched by cautious addition of sodium sulfate decahydrate until evolution of hydrogen had ceased. The suspension was stirred for 2 h, filtered through Dicalite and the residue washed thoroughly with ether. The filtrate and washings were combined and concentrated to yield (1-amino-cyclopropyl)methanol (180 mg, 98%) as a colourless oil.

The title compound was prepared using 5-cyano-1-(3-trifluoromethoxybenzyl)-1H-indole-2-carboxylic acid [prepared from 3-(trifluoromethoxy)benzyl bromide and ethyl 5-cyanoindole-2-carboxylate] and (1-amino-cyclopropyl)methanol in a manner similar to that described in Example 11.

$^1$H NMR (400 MHz, MeOD) $\delta_H$: 0.70-0.92 (m, 4H), 3.63 (s, 2H), 5.89 (s, 2H), 6.97 (br s, 1H), 7.05 (br d, 1H, J=7.9), 7.12 (br d, 1H, J=7.9), 7.23 (s, 1H), 7.35 (t, 1H, J=7.9), 7.52 (dd, 1H, J=8.8, 1.5), 7.60 (d, 1H, J=8.8), 8.11 (d, 1H, J=1.5);

EIMS: m/z=428.3 [M−H]$^-$.

Example 68

5-Cyano-1-(3-trifluoromethoxybenzyl)-1H-indole-2-carboxylic acid (1-hydroxymethyicyclopentylmethyl)amide

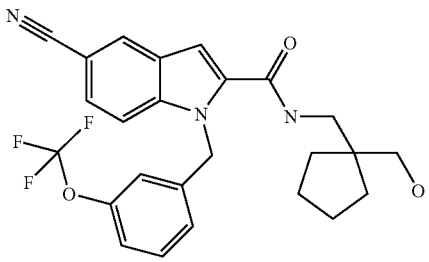

Ethyl cyanoacetate (2.50 g, 22 mmol) and 1,4-dibromobutane (5.00 g, 23.0 mmol) were dissolved in anhydrous DMF (20 ml) under nitrogen and cesium carbonate (21.0 g, 64 mmoles) added with water bath cooling. After stirring at room temperature for 18 h the reaction was diluted with water and extracted with ethyl acetate (2×80 ml), the organic layers were combined and washed with water (40 ml) and saturated aqueous sodium chloride solution (25 ml). The organics were dried over magnesium sulphate, filtered and evaporated under reduced pressure to give 1-cyano-cyclopentanecarboxylic acid ethyl ester as an almost colourless oil (3.64 g, 98%).

1-Cyano-cyclopentanecarboxylic acid ethyl ester (2.00 g, 12.0 mmol) was dissolved in anhydrous tetrahydrofuran (5 ml) under nitrogen and lithium aluminium hydride (36 ml, 36 mmoles, 1.0M in THF) was added dropwise at 0° C. After stirring at room temperature for 24 h water was carefully added to the reaction and the product mixture extracted with ethyl acetate (3×50 ml). The organic layers were combined and washed with water (40 ml) and saturated sodium chloride solution (25 ml). The combined organic phases were dried over magnesium sulphate, filtered and evaporated under reduced pressure to give 1-hydroxymethyl-cyclopentanecarbonitrile (75 mg, 28%) as an oil which solidified on standing to give a waxy yellow solid.

5-Cyano-1-(3-trifluoromethoxybenzyl)-1H-indole-2-carboxylic acid (200 mg, 0.56 mmol), 1-hydroxymethyl-cyclopentanecarbonitrile (145 mg, 1.12 mmol), 1-(3-dimethylaminopropyl)-3-ethyl carbodiimide hydrochloride (117 mg, 0.61 mmol) and 1-hydroxybenzotriazole hydrate (83 mg, 0.61 mmol) were stirred in DCM (20 ml) for 66 h at room temperature. The reaction was poured into water (25 ml) and diluted with DCM (25 ml). The organic layer was isolated using a hydrophobic filter tube and the DCM removed under reduced pressure and purified by semi-preparative HPLC followed by purification on neutral alumina giving the title compound (75 mg, 28%) as a glassy solid.

$^1$H NMR (400 MHz, CD$_3$CN) $\delta_H$: 1.38-1.44 (m, 4H), 1.57-1.70 (m, 4H), 3.22 (d, 2H, J=6.5), 3.34 (d, 2H, J=6.5), 3.65 (t, 1H, J=6.5), 5.90 (s, 2H), 6.99 (br s, 1H), 7.07 (d, 1H, J=7.9), 7.16-7.21 (m, 2H), 7.39 (t, 1H, J=7.9), 7.54-7.62 (m, 3H), 8.17-8.19 (m, 1H);

EIMS: m/z=472.1 (M+H)$^+$.

Example 69

5-Cyano-1-(3-trifluoromethoxybenzyl)-1H-indole-2-carboxylic acid (1-hydroxymethylcyclobutylmethyl)amide

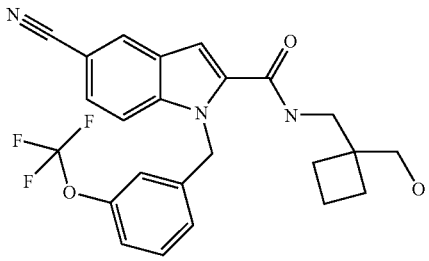

1-Cyano-cyclobutanecarboxylic acid ethyl ester was prepared from ethyl cyanoacetate (10.0 g, 88.4 mmol) and 1,3-dibromopropane (8.9 ml, 88.5 mmol) in the same manner as 1-cyano-cyclopentanecarboxylic acid ethyl ester giving 1-cyano-cyclobutanecarboxylic acid ethyl ester as a yellow oil (9.03 g, 67%).

1-Cyano-cyclobutanecarboxylic acid ethyl ester (2.00 g, 13.0 mmol) was dissolved in ethanol (30 ml) and treated with Raney Nickel (1 ml as a slurry in water) and hydrogen gas at 4 bar and heating at 40° C. for 18 h. The reaction mixture was filtered through Dicalite and washed through with ethanol (50 ml). The solvent was removed under reduced pressure to give 1-aminomethyl-cyclobutanecarboxylic acid ethyl ester as a yellow oil (1.47 g, 72%).

1-({[5-Cyano-1-(3-trifluoromethoxybenzyl)-1H-indole-2-carbonyl]amino}methyl)-cyclobutanecarboxylic acid ethyl ester was prepared from 1-aminomethyl-cyclobutanecarboxylic acid ethyl ester (262 mg, 1.65 mmol) and 5-cyano-1-(3-trifluoromethoxybenzyl)-1H-indole-2-carboxylic acid (400 mg, 1.10 mmol) in the same manner as 5-cyano-1-(3-trifluoromethoxybenzyl)-1H-indole-2-carboxylic acid (1-hydroxymethyl-cyclopentylmethyl)amide giving 1-({[5-cyano-1-(3-trifluoromethoxybenzyl)-1H-indole-2-carbonyl]amino}methyl)cyclobutanecarboxylic acid ethyl ester as a colourless gum (287 mg, 50%).

5-Cyano-1-(3-trifluoromethoxybenzyl)-1H-indole-2-carboxylic acid (1-hydroxymethyl-cyclobutylmethyl)amide was prepared from 1-({[5-cyano-1-(3-trifluoromethoxybenzyl)-1H-indole-2-carbonyl]amino}methyl)cyclobutanecarboxylic acid ethyl ester (267 mg, 0.52 mmol) in the same manner as 5-cyano-1-(3-trifluoromethoxybenzyl)-1H-indole-2-carboxylic acid (3-hydroxy-2-methylpropyl)amide giving, 5-cyano-1-(3-trifluoromethoxybenzyl)-1H-indole-2-carboxylic acid (1-hydroxymethylcyclobutylmethyl)amide as a colourless gum (74 mg, 30%).

$^1$H NMR (400 MHz, CDCl$_3$) $\delta_H$: 1.73-1.80 (m, 4H), 1.85-2.04 (m, 2H), 3.46 (s, 2H), 3.55 (d, 2H, J=6.3), 5.84 (s, 2H), 6.83 (br s, 1H), 6.99 (d, 1H, J=7.8), 7.04 (s, 1H), 7.06-7.14 (m, 2H), 7.30 (t, 1H, J=8.0), 7.40 (d, 1H, J=8.8), 7.50 (dd, 1H, J=8.8, 1.5), 7.99-8.02 (m, 1H);
EIMS: m/z=458.3 (M+H)$^+$.

Example 70

5-Cyano-1-(3-trifluoromethoxybenzyl)-1H-indole-2-carboxylic acid (3-hydroxy-2-methylpropyl)amide

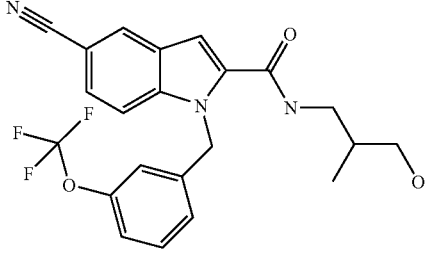

3-Aminoisobutyric acid (1.00 g, 9.7 mmol) was stirred in DCM under nitrogen and thionyl chloride (1.4 ml, 19.4 mmol) was added at room temperature. The reaction was heated to 50° C. for 2 h. The solvent and any excess thionyl chloride were removed under reduced pressure and the oil obtained was dissolved in ethanol (20 ml) stirring at room temperature for 18 h. The solvent was removed under reduced pressure to give 3-aminoisobutyric acid ethyl ester hydrochloride as a viscous, cloudy oil (1.47 g, 90%).

3-{[5-Cyano-1-(3-trifluoromethoxybenzyl)-1H-indole-2-carbonyl]amino}-2-methyl-propionic acid ethyl ester was prepared in the same manner as 5-cyano-1-(3-trifluoromethoxybenzyl)-1H-indole-2-carboxylic acid (1-hydroxymethyl-cyclopentylmethyl)amide from 5-cyano-1-(3-trifluoromethoxybenzyl)-1H-indole-2-carboxylic acid (300 mg, 83.3 mmol) and 3-aminoisobutyric acid ethyl ester, hydrochloride (168 mg, 0.10 mmol) giving 3-{[5-cyano-1-(3-trifluoromethoxybenzyl)-1H-indole-2-carbonyl]amino}-2-methylpropionic acid ethyl ester (204 mg, 51%).

3-{[5-Cyano-1-(3-trifluoromethoxybenzyl)-1H-indole-2-carbonyl]amino}-2-methylpropionic acid ethyl ester (170 mg, 0.36 mmol) was dissolved in dry tetrahydrofuran (10 ml) and lithium borohydride (28 mg, 1.28 mmol) was added and heated to reflux for 90 h. The reaction mixture was diluted with water and extracted with ethyl acetate (2×30 ml), the organic layers were combined and washed with water (20 ml) and saturated sodium chloride solution (20 ml). The organics were dried over magnesium sulphate, filtered and evaporated under reduced pressure to give 5-cyano-1-(3-trifluoromethoxybenzyl)-1H-indole-2-carboxylic acid (3-hydroxy-2-methylpropyl)amide as a pale yellow solid which was purified by preparative HPLC (75 mg, 48%).

$^1$H NMR (400 MHz, CDCl$_3$) $\delta_H$: 0.90-0.94 (d, 3H, J=6.8), 1.85-1.98 (m, 1H), 3.24-3.37 (m, 2H), 3.54-3.65 (m, 2H), 5.84 (s, 2H), 6.86 (br s, 1H), 6.91 (br t, 1H, J=5.9), 6.98 (br d, 1H, J=8.1), 7.00 (s, 1H), 7.09 (br d, 1H, J=8.1), 7.29 (t, 1H, J=8.1), 7.39 (d, 1H, J=8.8), 7.50 (dd, 1H, J=1.5, 8.8), 8.00-8.03 (m, 1H);
EIMS: m/z=432.1 (M+H)$^+$.

Example 71

5-Cyano-1-(3-trifluoromethoxybenzyl)-1H-indole-2-carboxylic acid (4,4,4-trifluoro-3-hydroxy-3-methyl-butyl)amide

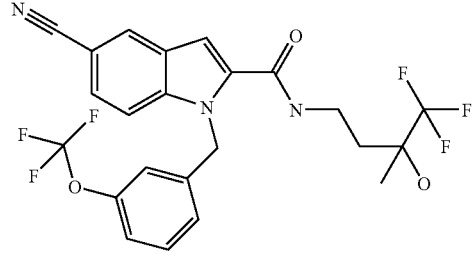

To a solution of 4,4,4-trifluoro-3-hydroxy-3-methylbutyric acid (1.81 g, 10.0 mmol) in methanol (10 ml) was added (trimethylsilyl)diazomethane (10 ml), dropwise. The reaction was then stirred at room temperature for 4 h. Removal of the solvent afforded the crude 3-(trifluoromethyl)-3-hydroxybutyric acid methyl ester as a yellow oil (1.92 g, 100%).

To a solution of the crude 4,4,4-trifluoro-3-hydroxy-3-methylbutyric acid (1.90 g, 10.0 mmol) in methanol (5 ml) was added concentrated aqueous ammonium hydroxide (10 ml), and the reaction stirred for 40 h at room temperature then evaporated to dryness to afford crude 4,4,4,-trifluoro-3-hydroxy-3-methyl butyramide (1.77 g, 100%) as a yellow oil.

A 1.0M solution of lithium aluminium hydride in tetrahydrofuran (30 ml, 30.0 mmol) was added dropwise to a solution of 4,4,4,-trifluoro-3-hydroxy-3-methyl butyramide (1.77 g, 10 mmol). The reaction was stirred at room temperature for 20 h, then quenched with water (1.2 ml), then 4M aqueous sodium hydroxide (1.2 ml), then water (3.6 ml). The inorganic salts were filtered off and the filtrate evaporated to dryness to yield 4-amino-1,1,1-trifluoro-2-methylbutan-2-ol (1.27 g, 81%) as a yellow solid.

The title compound was prepared using 5-cyano-1-(3-trifluoromethoxybenzyl)-1H-indole-2-carboxylic acid [prepared from 3-(trifluoromethoxy)benzyl bromide and ethyl 5-cyanoindole-2-carboxylate] and 4-amino-1,1,1-trifluoro-2-methylbutan-2-ol in a manner similar to that described in Example 11.

$^1$H NMR (400 MHz, CDCl$_3$) 1.43 (s, 3H), 1.89 (m, 1H), 2.05 (m, 1H), 2.72 (s, 1H), 3.57 (m, 1H), 3.72 (m, 1H), 5.84 (s, 2H), 6.85 (br s, 1H), 6.89 (s, 1H), 6.96 (s, 1H), 6.97 (d, 1H, J=7.8), 7.09 (d, 1H, J=8.0), 7.28 (t, J=8.0), 7.37 (d, 1H, J=7.5), 7.49 (d, 1H, J=7.5), 8.01 (s, 1H).
EIMS: m/z=500.0 (M+H)$^+$.

Example 72

5-Cyano-1-(3-trifluoromethoxybenzyl-1H-indole-2-carboxylic acid-(3-methoxy-2,2-dimethylpropyl) amide

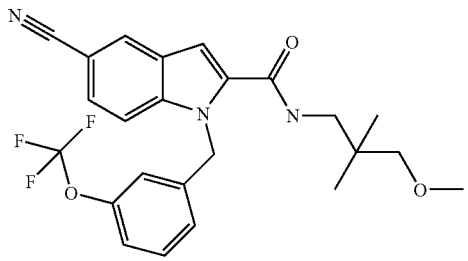

A stirred solution of isobutyronitrile (1.00 g, 14.5 mmol) in tetrahydrofuran (15 ml) was cooled to −70° C. 2.0M Lithium diisopropylamide (8.80 ml, 17.6 mmol) was then added dropwise over 10 min. The reaction mixture was stirred at −70° C. for 1 h, then chloromethyl methyl ether (1.33 ml, 17.5 mmol) in tetrahydrofuran (5 ml), was added dropwise. The cooling bath was removed and reaction mixture was stirred at room temperature for 1 h. Saturated aqueous ammonium chloride (10 ml) was added and the mixture extracted with DCM, washed with water (1×10 ml), brine (1×10 ml), dried with sodium sulfate and concentrated to low volume. Chromatography on silica using with heptane:diethyl ether (4:1) afforded 3-methoxy-2,2-dimethylpropionitrile (1.60 g, 98%) as a gum.

3-Methoxy-2,2-dimethylpropionitrile (1.60 g, 14.1 mmol), was dissolved in ethanol (100 ml), Raney nickel (50% slurry in water, 0.5 ml) added and the mixture hydrogenated for 3 h (50° C., 5 atm). The reaction mixture was cooled, filtered through dicalite and concentrated under reduced pressure to give 3-methoxy-2,2-dimethylpropylamine (440 mg, 27%), as a clear oil.

The title compound was prepared using 5-cyano-1-(3-trifluoromethoxybenzyl)-1H-indole-2-carboxylic acid [prepared from 3-(trifluoromethoxy)benzyl bromide and ethyl 5-cyanoindole-2-carboxylate]3-methoxy-2,2-dimethylpropylamine in a manner similar to that described in Example 11.

$^1$H NMR (400 MHz, CDCl$_3$): $\delta_H$ 0.95 (s, 6H), 3.25 (s, 2H), 3.34 (d, 2H, J=5.5), 3.41 (s, 3H), 5.87 (s, 2H), 6.91 (m, 2H), 6.99 (br d, 1H, J=8.2), 7.07 (br d, 1H, J=8.2), 7.27 (t, 1H, J=8.2), 7.33 (br t, 1H, J=5.5), 7.37 (d, 1H, J=8.6), 7.48 (dd, 1H, J=8.6, 1.8), 8.04 (br s, 1H);
EIMS: m/z=460.1 [M+H]$^+$.

Example 73

5-Cyano-1-(3-trifluoromethoxybenzyl-1H-indole-2-carboxylic acid-(4-ethoxy-2,2-dimethyl-butyl)amide

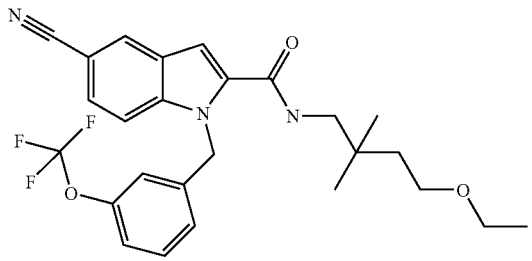

The title compound was prepared from 5-cyano-1-(3-trifluoromethoxybenzyl)-1H-indole-2-carboxylic acid and 4-ethoxy-2,2-dimethylbutylamine (prepared from chloroethyl ethyl ether and isobutyronitrile) using the procedure described for Example 72.

$^1$H NMR (400 MHz, CDCl$_3$): $\delta_H$ 0.91 (s, 6H), 1.21 (t, 3H, J=7.0), 1.55 (t, 2H, J=5.0), 3.25 (d, 2H, J=6.5), 3.49-3.56 (m, 4H), 5.88 (s, 2H), 6.89 (br s, 1H), 6.95 (s, 1H), 6.97 (br d, 1H, J=8.0), 7.07 (br d, 1H, J=8.0), 7.27 (t, 1H, J=8.0), 7.37 (d, 1H, J=8.7), 7.48 (dd, 1H, J=8.7, 1.4), 7.50 (br t, 1H, J=6.5), 8.02 (br s, 1H);
EIMS: m/z=488.3 [M+H]$^+$.

Example 74

5-Cyano-1-(3-trifluoromethoxybenzyl-1H-indole-2-carboxylic acid-[2,2-dimethyl-3-(tetrahydro-furan-2-yl)-propyl]amide

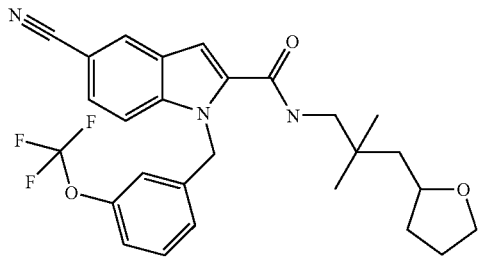

The title compound was prepared from 5-cyano-1-(3-trifluoromethoxybenzyl)-1H-indole-2-carboxylic acid and 2,2-dimethyl-3-(tetrahydro-furan-2-yl)propylamine (prepared from tetrahydrofurfuryl chloride and isobutyronitrile) using the procedure described for Example 72.

$^1$H NMR (400 MHz, CDCl$_3$): $\delta_H$ 0.93 (s, 3H), 0.93 (s, 3H), 1.43-1.60 (m, 3H), 1.85-2.09 (m, 3H), 3.20 (dd, 1H, J=13.5, 6.0), 3.35 (dd, 1H, J=13.5, 6.8), 3.81-3.89 (m, 1H), 3.89-4.02 (m, 2H), 5.90 (s, 2H), 6.89 (br s, 1H), 6.94 (s, 1H), 7.07 (br d, 1H, J=7.9), 7.06 (br d, 1H, J=7.9), 7.27 (t, 1H, J=7.9), 7.37 (d, 1H, J=8.8), 7.47 (dd, 1H, J=8.8, 1.5), 8.03 (s, 1H), 8.16 (br t, 1H, J=6.0);
EIMS: m/z=499.9 [M+H]$^+$.

Example 75

In-Vitro Determination of Efficacy and Potency at the Human CB1 Receptor Expressed in CHO Cells Chinese hamster ovary (CHO) cells, which stably express the human cannabinoid CB$_1$ receptor were co-transfected with a luciferase reporter gene which is under the regulatory control of an AP1-response element (AP1 luc). The cells were suspended in commercially available DMEM/F12 nut mix without phenol red, containing penicillin/streptomycin (50 U/50 μg/ml) and fungizone (1 μg/ml) before being seeded into white walled, white bottomed 96 well plates at a density of 3×10$^4$ cells per well (100 μl final volume) and incubated overnight (approximately 18 hrs at 37° C., 5% CO$_2$ in air) prior to assay.

The test compounds (10 mM solution in DMSO) were diluted in DMEM/F12 nut mix (w/o phenol red) containing 3% bovine serum albumin to give a concentration range of 0.1 mM to 1 nM. 10 μl of each dilution was added to the relevant wells in the cell plate to give a final concentration range of 10 μM to 0.1 nM. Five minutes after the addition of compounds, 10 μl of 1 μM CP-55,940 was added to all wells except control wells.

Plates were incubated for 5 hours at 37° C. before addition of 100 μl LucLite reagent to each well (reconstituted as per manufacturer's instructions). Plates were sealed with Top Seal and counted on the Packard TopCount (single photon counting, 0.01 minute count time, no count delay).

Following stimulation of the $CB_1$ receptor, luciferase expression is enhanced and this can be measured as an increase in enzyme activity. This reporter system is therefore used as a functional test to evaluate the potency of antagonist compounds at the $CB_1$ receptor. Data was analysed using curve fitting and a minimum sum of squares method to produce pEC50 values.

Table 1 indicates the potency of the representative compounds of the invention.

TABLE 1

| Example | Chemical name | Potency |
|---|---|---|
| 16 | 5-Chloro-1-(3-trifluoromethoxybenzyl)-1H-indole-2-carboxylic acid (3-isopropoxypropyl)amide | (+) |
| 23 | 5-Cyano-1-(2-methoxy-5-trifluoromethoxybenzyl)-1H-indole-2-carboxylic acid (3-hydroxy-2,2-dimethylpropyl)amide | (++) |
| 35 | trans-5-Cyano-1-(3-trifluoromethoxybenzyl)-1H-indole-2-carboxylic acid (2-hydroxy-cyclohexylmethyl)amide | (+++) |
| 48 | trans-5-Cyano-1-[3-(4-methyl-piperazin-1-yl)-benzyl]-1H-indole-2-carboxylic acid (2-hydroxy-cyclohexylmethyl)amide | (+) |
| 55 | trans-5-Cyano-1-(3-trifluoromethoxybenzyl)-1H-indole-2-carboxylic acid (2-hydroxy-cyclopentyl)amide | (++) |
| 61 | 5-Cyano-1-(3-trifluoromethoxybenzyl)-1H-indole-2-carboxylic acid (1-hydroxy-cyclohexylmethyl)amide | (++) |
| 65 | 5-Cyano-1-(2-methyl-5-trifluoromethylbenzyl)-1H-indole-2-carboxylic acid (3-hydroxy-3-methylbutyl)amide | (++) |
| 66 | 5-Cyano-1-(3-trifluoromethoxybenzyl)-1H-indole-2-carboxylic acid (1-hydroxy-cyclopentylmethyl)amide | (++) |
| 69 | 5-Cyano-1-(3-trifluoromethoxybenzyl)-1H-indole-2-carboxylic acid (1-hydroxymethylcyclopentylmethyl)amide | (+++) |
| 72 | 5-Cyano-1-(3-trifluoromethoxybenzyl)-1H-indole-2-carboxylic acid (4,4,4-trifluoro-3-hydroxy-3-methylbutyl)amide | (++) |

(+++) $pIC_{50}$ >9
(++) $pIC_{50}$ 8-9
(+) $pIC_{50}$ 7-8

What is claimed:

1. A 1-benzylindole-2-carboxamide compound of formula I,

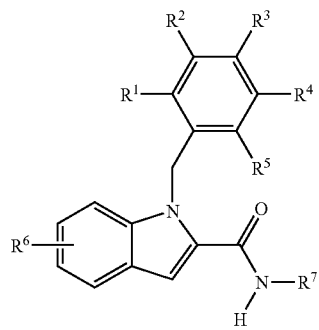

Formula I wherein $R^1$ is H or F;

$R^2$ is H, halogen, $C_{1-4}$alkyl, $C_{1-4}$alkyloxy, $C_{3-6}$cycloalkyl or $C_{3-6}$cycloalkyl$C_{1-2}$alkyl, said $C_{1-4}$alkyl and $C_{1-4}$alkyloxy being optionally substituted with one to three halogens or $R^2$ is a five or six membered heteroaryl ring comprising one or two heteroatoms selected from N and O or $R^2$ is a five or six membered saturated heterocyclic ring comprising one or two heteroatomic moieties selected from O and $NR^8$;

$R^3$ is H or F;

$R^4$ is H, halogen, $CH_3$, $OCH_3$ or $CF_3$ or together with $R^5$ and the phenyl ring $R^4$ forms an indol-4-yl or a quinolin-5-yl;

$R^5$ is H, halogen, $C_{1-4}$alkyl, $CF_3$, $C_{1-4}$alkyloxy, $OCF_3$ or together with $R^4$ and the phenyl ring $R^5$ forms an indol-4-yl or a quinolin-5-yl;

provided that one to three of $R^1$-$R^5$ are not H;

$R^6$ is one or two substituents selected from Cl, Br and CN;

$R^7$ is $C_{1-6}$alkyl optionally substituted with one to three halogens, $C_{3-6}$cycloalkyl or $C_{3-6}$cycloalkyl$C_{1-2}$alkyl each being substituted with 1-2 substituents selected from hydroxy, hydroxy$C_{1-2}$alkyl, $C_{1-4}$alkyloxy and $C_{1-2}$thioalkyloxy, or $R^7$ is $C_{4-6}$oxacycloalkyl$C_{1-2}$alkyl, said $C_{1-2}$alkyl being optionally substituted with hydroxy or hydroxy$C_{1-2}$alkyl or $R^7$ is $C_{4-6}$oxacycloalkyl and $R^8$ is H, $C_{1-4}$alkyl or $C_{1-4}$acyl or a pharmaceutically acceptable salt thereof.

2. The 1-benzylindole-2-carboxamide compound according to claim 1, wherein $R^1$, $R^3$ and $R^4$ are H.

3. The 1-benzylindole-2-carboxamide compound according to claim 1, wherein $R^2$ is $CH_3$, $CH(CH_3)_3$, $CF_3$, $OCH_3$, $OCH(CH_3)_2$, $OCHF_2$, $OCF_3$, Br, Cl or F.

4. The 1-benzylindole-2-carboxamide compound according to claim 1, wherein $R^5$ is H, $CH_3$, $OCH_3$, $OCF_3$, Cl or F.

5. The 1-benzylindole-2-carboxamide compound according to claim 1, wherein $R^6$ is CN.

6. The 1-benzylindole-2-carboxamide compound according to claim 1, wherein $NHR^7$ is a group selected from

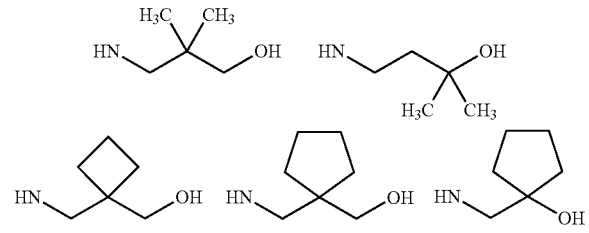

-continued

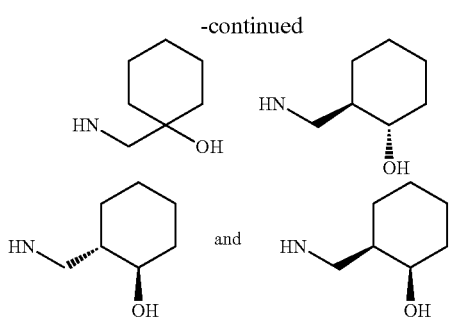

7. A 1-benzylindole-2-carboxamide compound selected from:
   5-chloro-1-(2,5-dimethylbenzyl)-1H-indole-2-carboxylic acid (3-hydroxy-2,2-dimethylpropyl)amide;
   5-chloro-1-(2,5-bis-trifluoromethylbenzyl)-1H-indole-2-carboxylic acid (3-hydroxy-2,2-dimethylpropyl)amide;
   5-chloro-1-(2-methoxy-5-trifluoromethoxybenzyl)-1H-indole-2-carboxylic acid (3-hydroxy-2,2-dimethylpropyl)amide;
   5-cyano-1-(2-methoxy-5-trifluoromethoxybenzyl)-1H-indole-2-carboxylic acid (3-hydroxy-2,2-dimethylpropyl)amide;
   5-cyano-1-(3-trifluoromethoxybenzyl)-1H-indole-2-carboxylic acid (3-hydroxy-2,2-dimethylpropyl)amide;
   trans-5-cyano-1-(3-trifluoromethoxybenzyl)-1H-indole-2-carboxylic acid (2-hydroxy-cyclohexylmethyl)amide;
   5-cyano-1-(5-bromo-2-methoxybenzyl)-1H-indole-2-carboxylic acid (3-hydroxy-2,2-dimethylpropyl)amide;
   5-cyano-1-(5-tert-butyl-2-methoxybenzyl)-1H-indole-2-carboxylic acid (3-hydroxy-2,2-dimethylpropyl)amide;
   5-cyano-1-(2-methoxy-5-methylbenzyl)-1H-indole-2-carboxylic acid (3-hydroxy-2,2-dimethylpropyl)amide;
   5-cyano-1-(5-chloro-2-methoxybenzyl)-1H-indole-2-carboxylic acid (3-hydroxy-2,2-dimethylpropyl)amide;
   5-cyano-1-(2-methyl-5-trifluoromethylbenzyl)-1H-indole-2-carboxylic acid (3-hydroxy-3-methylbutyl)amide;
   5-cyano-1-(3-trifluoromethoxybenzyl)-1H-indole-2-carboxylic acid (1-hydroxymethylcyclopentylmethyl)amide; and
   5-cyano-1-(3-trifluoromethoxybenzyl)-1H-indole-2-carboxylic acid (1-hydroxymethylcyclobutyl-methyl)amide,
   or a pharmaceutically acceptable salt thereof.

8. A pharmaceutical composition comprising a 1-benzylindole-2-carboxamide compound according to claim 1 or a pharmaceutically acceptable salt thereof in admixture with one or more pharmaceutically acceptable excipients.

9. A method for the treatment or prevention of obesity, the method comprising administering to a subject in need thereof an effective amount of the 1-benzylindole-2-carboxamide compound according to claim 1 or a pharmaceutically acceptable salt thereof.

10. A method for the treatment or prevention of nicotine dependence, the method comprising administering to a subject in need thereof an effective amount of the 1-benzylindole-2-carboxamide compound according to claim 1 or a pharmaceutically acceptable salt thereof.

11. A method for the treatment or prevention of obesity, the method comprising administering to a subject in need thereof an effective amount of the 1-benzylindole-2-carboxamide compound according to claim 1 or a pharmaceutically acceptable salt thereof.

12. A method for the treatment or prevention of nicotine dependence, the method comprising administering to a subject in need thereof an effective amount of the 1-benzylindole-2-carboxamide compound according to claim 7 or a pharmaceutically acceptable salt thereof.

13. A pharmaceutical composition comprising a 1-benzylindole-2-carboxamide compound according to claim 7 or a pharmaceutically acceptable salt thereof in admixture with one or more pharmaceutically acceptable excipients.

* * * * *